(12) United States Patent
Bae et al.

(10) Patent No.: US 11,944,359 B2
(45) Date of Patent: Apr. 2, 2024

(54) ADJUSTABLE IMPLANT, SYSTEM AND METHODS

(71) Applicant: Nuvasive Specialized Orthopedics, Inc., San Diego, CA (US)

(72) Inventors: Youngsam Bae, Aliso Viejo, CA (US); Khoa Pham, Garden Grove, CA (US); Niels Smidth, Laguna Beach, CA (US); Everett Van Zuiden, Chula Vista, CA (US); Dave Emerson, Chelmsford, CA (US)

(73) Assignee: Nuvasive Specialized Orthopedics, Inc., San Diego, CA (US)

( * ) Notice: Subject to any disclaimer, the term of this patent is extended or adjusted under 35 U.S.C. 154(b) by 0 days.

(21) Appl. No.: 17/651,589

(22) Filed: Feb. 18, 2022

(65) Prior Publication Data

US 2022/0265325 A1  Aug. 25, 2022

Related U.S. Application Data

(60) Provisional application No. 63/152,562, filed on Feb. 23, 2021.

(51) Int. Cl.
*A61B 17/72* (2006.01)
*G16H 20/40* (2018.01)
(Continued)

(52) U.S. Cl.
CPC ......... *A61B 17/7216* (2013.01); *G16H 20/40* (2018.01); *A61B 2017/00022* (2013.01);
(Continued)

(58) Field of Classification Search
CPC ........ A61B 17/72–17/7291; A61B 2562/0252; A61B 2562/0247; A61B 2562/0261;
(Continued)

(56) References Cited

U.S. PATENT DOCUMENTS 2,702,031 A   2/1955  Wenger
3,111,945 A  11/1963  Von Solbrig
(Continued)

FOREIGN PATENT DOCUMENTS

CN      1697630 A   11/2005
CN    101040807 A    9/2007
(Continued)

OTHER PUBLICATIONS

Abe et al., "Experimental external fixation combined with percutaneous discectomy in the management of scoliosis.", Spine, 1999, pp. 646-653, 24, No. 7.
(Continued)

*Primary Examiner* — Julianna N Harvey

(57) ABSTRACT

Aspects of the disclosure relate to an adjustable implant configured to be implanted into a patient that includes an adjustable portion moveable relative to a housing. The adjustable implant may include various smart components for enhancing operation of the implant. Smart components may include a controller for managing operations and a transducer for communicating ultrasound data with an external interface device. Additional smart components may include a load cell within the housing for measuring an imparted load; a sensor for measuring angular position of the adjustable portion; a dual sensor arrangement for measuring imparted forces; a reed switch; a half piezo transducer; and an energy harvester.

38 Claims, 14 Drawing Sheets

(51) Int. Cl.
    *A61B 17/00*     (2006.01)
    *A61B 17/56*     (2006.01)
    *A61B 17/68*     (2006.01)

(52) U.S. Cl.
    CPC ............ *A61B 2017/00039* (2013.01); *A61B 2017/0011* (2013.01); *A61B 2017/00137* (2013.01); *A61B 2017/00221* (2013.01); *A61B 2017/00362* (2013.01); *A61B 2017/00402* (2013.01); *A61B 2017/00411* (2013.01); *A61B 2017/00477* (2013.01); *A61B 2017/00876* (2013.01); *A61B 2017/00991* (2013.01); *A61B 2017/564* (2013.01); *A61B 2017/681* (2013.01); *A61B 2560/0219* (2013.01); *A61B 2562/0252* (2013.01); *A61B 2562/0261* (2013.01)

(58) Field of Classification Search
    CPC .......... A61B 2562/0266; A61B 17/70–17/707; A61B 17/80–17/8076
    See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,304,210 A | 4/1994 | Crook |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,456,724 A | 10/1995 | Yen et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,120,502 A | 9/2000 | Michelson |
| 6,120,509 A | 9/2000 | Michelson et al. |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,488 B1 | 12/2002 | Hunter et al. |
| 6,499,907 B1 | 12/2002 | Baur |
| 6,500,110 B1 | 12/2002 | Davey et al. |
| 6,508,820 B2 | 1/2003 | Bales |

(56) References Cited

U.S. PATENT DOCUMENTS

| | | |
|---|---|---|
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,605,089 B1 | 8/2003 | Michelson |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,005 B2 | 3/2004 | Roy et al. |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,007,699 B2 | 3/2006 | Martinelli et al. |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,594 B2 | 2/2007 | Biscup |
| 7,182,736 B2 | 2/2007 | Roy et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,351,244 B2 | 4/2008 | Hamada |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,455,672 B2 | 11/2008 | Michelson |
| 7,458,981 B2 | 12/2008 | Fielding et al. |
| 7,485,149 B1 | 2/2009 | White |
| 7,489,495 B2 | 2/2009 | Stevenson |
| 7,491,179 B2 | 2/2009 | Roy et al. |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,615,070 B2 | 11/2009 | Biscup |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,756,579 B2 | 7/2010 | Nitzan et al. |
| 7,762,998 B2 | 7/2010 | Birk et al. |
| 7,763,075 B2 | 7/2010 | Navarro et al. |
| 7,763,076 B2 | 7/2010 | Navarro et al. |
| 7,763,080 B2 | 7/2010 | Southworth |
| 7,766,855 B2 | 8/2010 | Miethke |
| 7,771,478 B2 | 8/2010 | Navarro et al. |
| 7,771,480 B2 | 8/2010 | Navarro et al. |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,794,499 B2 | 9/2010 | Navarro et al. |
| 7,806,935 B2 | 10/2010 | Navarro et al. |
| 7,811,328 B2 | 10/2010 | Molz, IV et al. |
| 7,822,465 B2 | 10/2010 | Carls et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,955,357 B2 | 1/2011 | Kiester |
| 7,878,988 B2 | 2/2011 | Bush et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,981,144 B2 | 4/2011 | Geist et al. |
| 7,935,116 B2 | 5/2011 | Michelson |
| 7,938,831 B2 | 5/2011 | Leroux et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 7,993,269 B2 | 8/2011 | Donofrio et al. |
| 8,002,809 B2 | 8/2011 | Baynham |
| 8,011,308 B2 | 9/2011 | Picchio |
| 8,016,859 B2 | 9/2011 | Donofrio et al. |
| 8,026,729 B2 | 9/2011 | Kroh et al. |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,695 B2 | 12/2011 | Gupta et al. |
| 8,075,601 B2 | 12/2011 | Young |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,206,387 B2 | 6/2012 | Michelson |

(56) References Cited

U.S. PATENT DOCUMENTS

| | | |
|---|---|---|
| 8,211,149 B2 | 7/2012 | Justis |
| 8,211,151 B2 | 7/2012 | Schwab et al. |
| 8,216,279 B2 | 7/2012 | Bruneau et al. |
| 8,221,420 B2 | 7/2012 | Keller |
| 8,226,690 B2 | 7/2012 | Altarac et al. |
| 8,236,002 B2 | 8/2012 | Fortin et al. |
| 8,237,451 B2 | 8/2012 | Joy et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,343,153 B2 | 1/2013 | Duda et al. |
| 8,343,192 B2 | 1/2013 | Kiester |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,388,553 B2 | 3/2013 | James et al. |
| 8,394,124 B2 | 3/2013 | Biyani |
| 8,403,958 B2 | 3/2013 | Schwab |
| 8,414,584 B2 | 4/2013 | Brigido |
| 8,419,734 B2 | 4/2013 | Walker et al. |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,551,092 B2 | 10/2013 | Morgan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,570,187 B2 | 10/2013 | Janna et al. |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,622,936 B2 | 1/2014 | Schenberger et al. |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,685,093 B2 | 4/2014 | Anderson et al. |
| 8,690,888 B2 | 4/2014 | Stein et al. |
| 8,709,090 B2 | 4/2014 | Makower et al. |
| 8,721,570 B2 | 5/2014 | Gupta et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,877 B2 | 7/2014 | Stein et al. |
| 8,777,947 B2 | 7/2014 | Zahrly et al. |
| 8,777,995 B2 | 7/2014 | McClintock et al. |
| 8,784,339 B2 | 7/2014 | Stein et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,852,236 B2 | 10/2014 | Kiester |
| 8,870,881 B2 | 10/2014 | Rezach et al. |
| 8,870,959 B2 | 10/2014 | Arnin |
| 8,896,324 B2 | 11/2014 | Kroh et al. |
| 8,906,091 B2 | 12/2014 | Duda et al. |
| 8,911,448 B2 | 12/2014 | Stein |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,926,674 B2 | 1/2015 | Wolter et al. |
| 8,945,133 B2 | 2/2015 | Stein et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,743 B2 | 6/2015 | Munro et al. |
| 9,060,810 B2 | 6/2015 | Kercher et al. |
| 9,078,703 B2 | 7/2015 | Arnin |
| 9,107,580 B2 | 8/2015 | Goguin et al. |
| 9,278,214 B2 | 3/2016 | Young |
| 9,320,617 B2 | 4/2016 | Abdou et al. |
| 9,445,720 B2 | 9/2016 | Janna et al. |
| 9,510,785 B2 | 12/2016 | Munro et al. |
| RE46,582 E | 10/2017 | Morgan et al. |
| 9,795,423 B2 | 10/2017 | Deirmengian et al. |
| 9,820,869 B2 | 11/2017 | Aryan |
| 9,839,374 B2 | 12/2017 | Roche et al. |
| 10,117,580 B1 | 11/2018 | Puryear et al. |
| 10,123,881 B2 | 11/2018 | Moskowitz et al. |
| 10,271,832 B2 | 4/2019 | O'Neil et al. |
| 10,271,833 B2 | 4/2019 | Sengun |
| 10,292,831 B2 | 5/2019 | Zellmer et al. |
| 10,441,210 B2 | 10/2019 | Deirmengian et al. |
| 10,524,718 B2 | 1/2020 | Young |
| 10,595,771 B2 | 3/2020 | Deirmengian et al. |
| 10,617,880 B2 | 4/2020 | Zellmer et al. |
| 10,639,167 B2 | 5/2020 | Benson et al. |
| 10,675,069 B2 | 6/2020 | Deirmengian et al. |
| 10,702,189 B2 | 7/2020 | Droit et al. |
| 10,765,527 B2 | 9/2020 | Chin et al. |
| 10,940,025 B2 | 3/2021 | O'Neil et al. |
| 10,952,867 B2 | 3/2021 | Moskowitz et al. |
| 11,058,549 B2 | 7/2021 | Zellmer et al. |
| 11,123,197 B2 | 9/2021 | Gross |
| 11,298,162 B2 | 4/2022 | Benson et al. |
| 11,304,819 B2 | 4/2022 | Chevalier |
| 2002/0049394 A1 | 4/2002 | Roy et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0083746 A1 | 5/2003 | Kuslich |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stanch et al. |
| 2004/0055610 A1 | 3/2004 | Forsell |
| 2004/0073221 A1 | 4/2004 | Biscup |
| 2004/0133219 A1 | 7/2004 | Forsell |
| 2004/0138725 A1 | 7/2004 | Forsell |
| 2004/0193266 A1 | 9/2004 | Meyer |
| 2004/0243130 A1 | 12/2004 | Biscup |
| 2005/0010301 A1 | 1/2005 | Disilvestro et al. |
| 2005/0034705 A1 | 2/2005 | McClendon |

(56) References Cited

U.S. PATENT DOCUMENTS

| | | |
|---|---|---|
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1* | 3/2006 | Morgan ............... A61B 17/80 606/60 |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0247773 A1 | 11/2006 | Stamp |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0133016 A1 | 6/2008 | Heinz |
| 2008/0147125 A1* | 6/2008 | Colleran ............ A61B 17/8004 606/280 |
| 2008/0154265 A1 | 6/2008 | Duda et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0208516 A1 | 8/2008 | James |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0098092 A1 | 4/2009 | Meredith |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0222050 A1* | 9/2009 | Wolter ............... A61B 5/0031 600/587 |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249533 A1 | 9/2010 | Pierce et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0268119 A1 | 10/2010 | Morrison |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2011/0295159 A1 | 12/2011 | Shachar et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0065497 A1 | 3/2012 | Brown et al. |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0253345 A1 | 10/2012 | Wixted |
| 2012/0271353 A1 | 10/2012 | Barry |
| 2012/0289865 A1 | 11/2012 | Lambrecht et al. |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0079678 A1 | 3/2013 | Stein et al. |
| 2013/0123847 A1 | 5/2013 | Anderson et al. |

(56) References Cited

U.S. PATENT DOCUMENTS

| | | |
|---|---|---|
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0150970 A1 | 6/2013 | Thaiyananthan |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2016/0113683 A1 | 4/2016 | Cheng |
| 2016/0270927 A1 | 9/2016 | Zellmer et al. |
| 2016/0367297 A1 | 12/2016 | Nill et al. |
| 2017/0007420 A1 | 1/2017 | Stevenson et al. |
| 2017/0079555 A1 | 3/2017 | Munro et al. |
| 2017/0172624 A1 | 6/2017 | Brunner et al. |
| 2017/0196508 A1 | 7/2017 | Hunter |
| 2017/0231559 A1 | 8/2017 | Cuevas et al. |
| 2018/0055444 A1* | 3/2018 | Windolf ............ A61B 17/80 |
| 2018/0153709 A1 | 6/2018 | Hunter |
| 2018/0192939 A1 | 7/2018 | Roth et al. |
| 2018/0318579 A1 | 11/2018 | Puryear et al. |
| 2019/0008386 A1 | 1/2019 | Puryear et al. |
| 2019/0009083 A1 | 1/2019 | Webster et al. |
| 2019/0150835 A1 | 5/2019 | Bae |
| 2019/0156482 A1 | 5/2019 | Deitz et al. |
| 2019/0224022 A1 | 7/2019 | Zellmer et al. |
| 2019/0365541 A1 | 12/2019 | Friis et al. |
| 2020/0022733 A1 | 1/2020 | Benson et al. |
| 2020/0022772 A1 | 1/2020 | Benson et al. |
| 2020/0069247 A1 | 3/2020 | Hunter |
| 2020/0253588 A1 | 3/2020 | Bae et al. |
| 2020/0107940 A1 | 4/2020 | Murphy et al. |
| 2020/0108252 A1 | 4/2020 | Zellmer et al. |
| 2020/0187849 A1 | 6/2020 | Deirmengian et al. |
| 2020/0253651 A1 | 8/2020 | Deirmengian et al. |
| 2020/0297513 A1 | 9/2020 | Zeller et al. |
| 2020/0352723 A1 | 11/2020 | Jimenez et al. |
| 2021/0052394 A1 | 2/2021 | Chin et al. |
| 2021/0077216 A1* | 3/2021 | Ledet ................ A61B 90/06 |
| 2021/0101002 A1 | 4/2021 | Saigal et al. |
| 2021/0128919 A1 | 5/2021 | Zellmer et al. |
| 2021/0161682 A1 | 6/2021 | O'Neil et al. |
| 2021/0205625 A1 | 7/2021 | Friis et al. |
| 2021/0243899 A1 | 8/2021 | Harris et al. |
| 2021/0315708 A1 | 10/2021 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1240873 A2 | 9/2002 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | 2006/010933 A1 | 2/2006 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |
| WO | 2016/172806 A1 | 11/2016 |
| WO | 2020/055874 A1 | 3/2020 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

(56) References Cited

OTHER PUBLICATIONS

Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany, (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering•General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010-2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.

(56) References Cited

OTHER PUBLICATIONS

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work?.", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany, (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "VEPTR Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

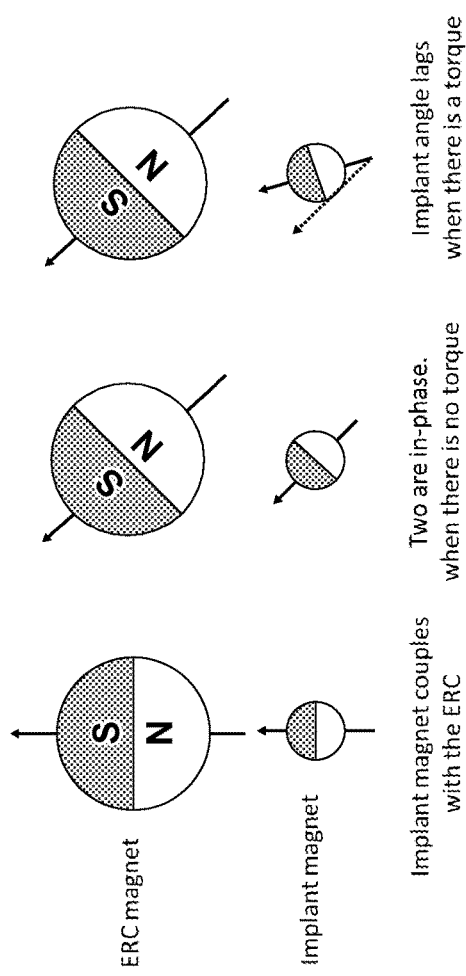
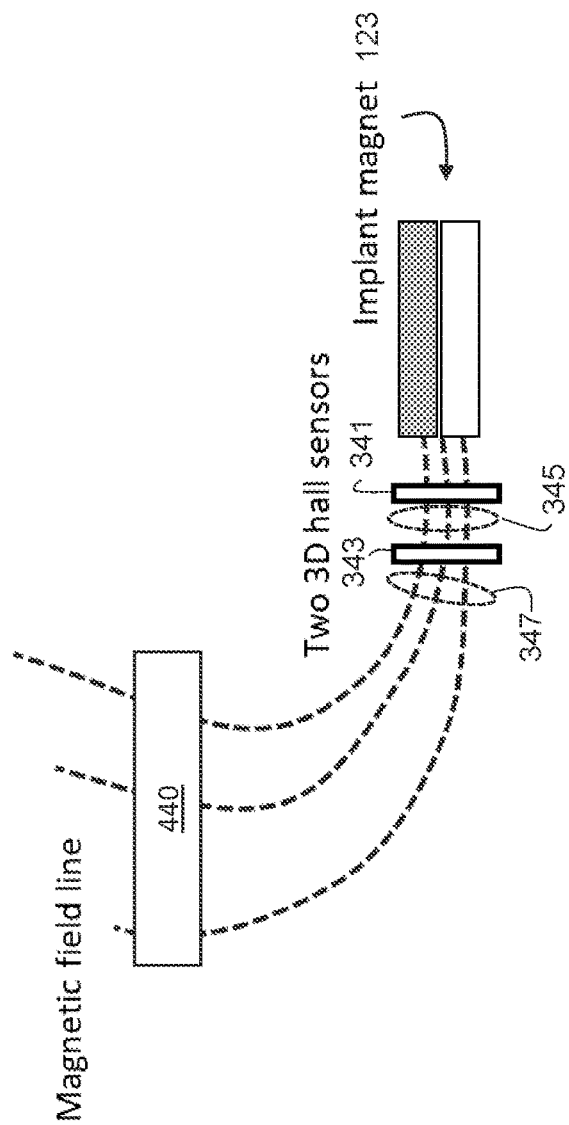
FIG. 12

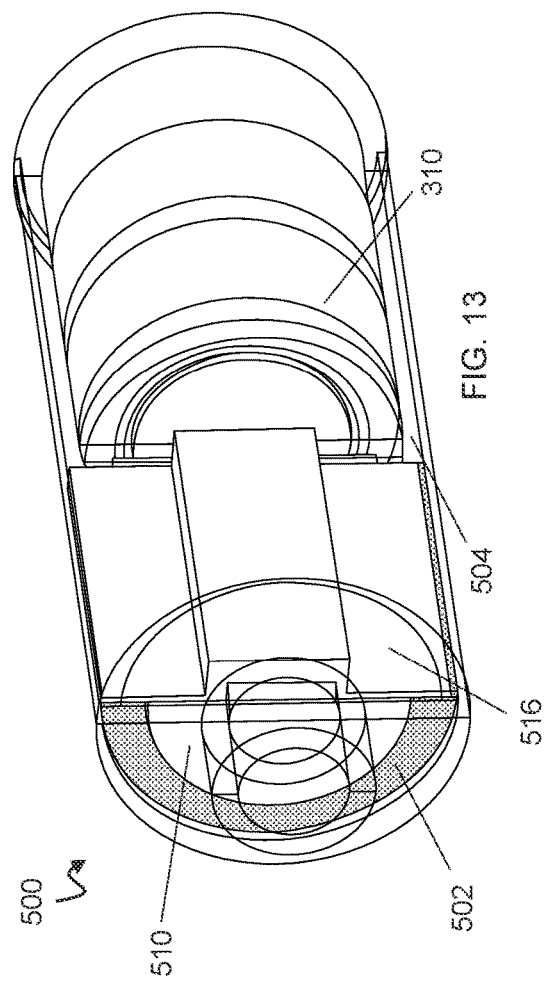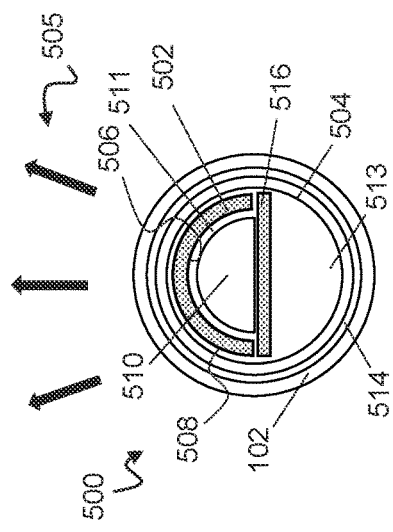

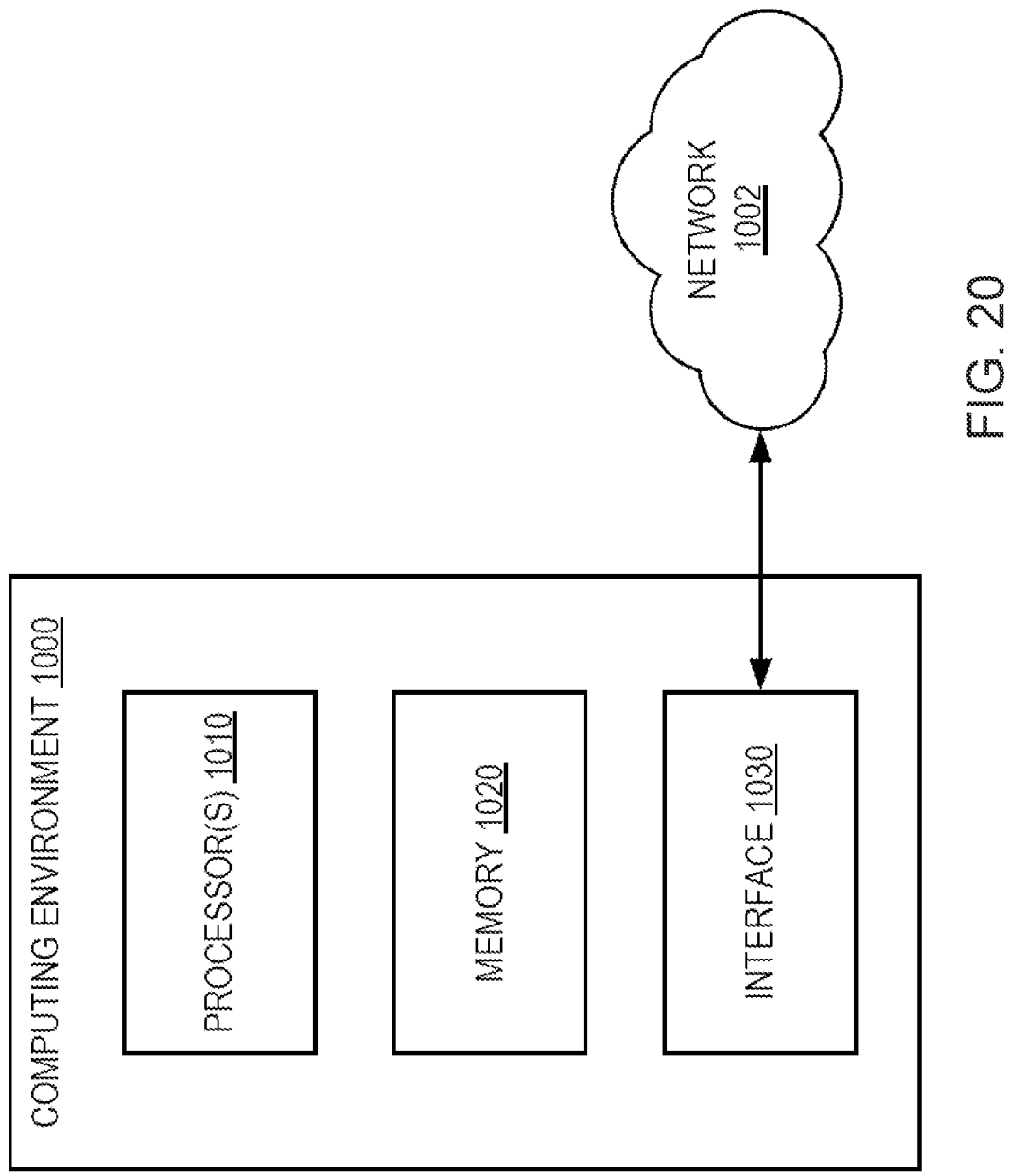

ADJUSTABLE IMPLANT, SYSTEM AND METHODS

CROSS REFERENCE TO RELATED APPLICATIONS

The present application claims the benefit of U.S. Provisional Application No. 63/152,562, filed Feb. 23, 2021.

TECHNICAL FIELD

The subject matter described herein relates to an adjustable implant, an adjustable implant system and associated methods.

BACKGROUND

Distraction osteogenesis is a technique which has been used to grow new bone in patients with a variety of defects. For example, limb lengthening is a technique in which the length of a bone (for example a femur or tibia) may be increased. By creating a corticotomy, or osteotomy, in the bone, which is a cut through the bone, the two resulting sections of bone may be moved apart at a particular rate, such as one (1.0) mm per day, allowing new bone to regenerate between the two sections as they move apart. This technique of limb lengthening is used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibia to increase the patient's height.

Limb lengthening is often performed using external fixation, wherein an external distraction frame is attached to the two sections of bone by pins which pass through the skin. The pins can be sites for infection and are often painful for the patient, as the pin placement site remains a somewhat open wound "pin tract" throughout the treatment process. The external fixation frames are also bulky, making it difficult for patient to comfortably sit, sleep and move. Intramedullary lengthening devices also exist, such as those described in U.S. Patent Application Publication No. 2011/0060336, which is incorporated by reference herein.

SUMMARY

A first aspect of the disclosure relates to an adjustable implant configured to be implanted into a patient. The adjustable implant may include: an adjustable portion moveable relative to the housing; and a load cell within the housing for measuring a load imparted on the implant during movement of the adjustable portion relative to the housing or during movement of a bone relative to the housing.

A second aspect of the disclosure relates to a method. The method includes: adjusting an adjustable implant having: a housing; an adjustable portion moveable relative to the housing; and a load cell within the housing for measuring a load; and measuring, with the load cell, the load imparted on the implant during movement of the adjustable portion relative to the housing or during movement of a bone relative to the housing.

A third aspect of the disclosure relates to an adjustable implant. The adjustable implant includes: a housing; an adjustable portion movable relative to the housing; an actuator positioned within the housing and configured to cause movement of the adjustable portion relative to the housing; and a sensor positioned adjacent to the actuator and configured to monitor an angular position of the actuator.

A fourth aspect of the disclosure relates to a method. The method includes: adjusting an adjustable implant, the adjustable implant including: a housing; an adjustable portion moveable relative to the housing; an actuator positioned within the housing and configured to cause movement of the adjustable portion relative to the housing; and a sensor positioned adjacent to the actuator and configured to monitor an angular position of the actuator; sensing, via the sensor, an angular position of the actuator; and calculating a distraction length or a compression length of the adjustable implant based upon the number of rotations of the actuator.

A fifth aspect of the disclosure relates to an adjustable implant. The adjustable implant includes: a housing; an adjustable portion moveable relative to the housing; a first actuator configured to cause movement of the adjustable portion relative to the housing, the first actuator being actuated by an external adjustment device having a second actuator therein; a first sensor configured to measure a position of the first actuator; and a second sensor configured to measure a position of the second actuator within the external adjustment device.

A sixth aspect of the disclosure relates to a method. The method includes: adjusting an adjustable implant, the adjustable implant having a housing and an adjustable portion moveable relative to the housing; measuring a position of a first actuator of the adjustable implant, the first actuator being configured to cause movement of the adjustable portion relative to the housing; measuring a position of a second actuator of an external adjustment device, the external adjustment device configured to actuate the first actuator of the adjustable implant; and determining at least one of a distraction force, a distraction torque, a compression force, and a compression length based on the position of the first actuator and the position of the second actuator at a given time.

A seventh aspect of the disclosure relates to an adjustable implant. The adjustable implant includes: a housing; an adjustable portion moveable relative to the housing; a first actuator configured to cause movement of the adjustable portion relative to the housing, the first actuator being actuated by an external adjustment device having a second actuator therein; a first sensor located at a first position in the housing configured to measure a first magnetic field of the first actuator relative to the second actuator; a second sensor located at a second position in the housing configured to measure a second magnetic field of the first actuator relative to the second actuator; and a controller that determines at least one force by analyzing the first magnetic field and the second magnetic field.

An eighth aspect of the disclosure relates to a method. The method includes: adjusting an adjustable implant, the adjustable implant having a housing and an adjustable portion, the adjustable implant having a first actuator configured to cause movement of the adjustable portion relative to the housing in response to movement of a second actuator of an external adjustment device; using a first sensor positioned at a first location in the housing to measure a first magnetic field of the first actuator of the adjustable implant relative to the second actuator; using a second sensor positioned at a second location in the housing to measure a second magnetic field of the first actuator of the adjustable implant relative to the second actuator; and determining at least one force by analyzing the first magnetic field and the second magnetic field.

A ninth aspect of the disclosure relates to a signal transmission device. The signal transmission device includes: a housing; a half-cylinder piezoelectric transducer positioned within the housing and having an inner diameter and an outer diameter; a metal backing positioned adjacent the inner diameter; and a semiconductor package positioned within the housing and substantially surrounding the half-cylinder piezoelectric transducer and the metal backing.

A tenth aspect of the disclosure relates to an adjustable implant. The adjustable implant included: an implant housing; and a signal transmission device positioned within the implant housing, the signal transmission device including: a half-cylinder piezoelectric transducer having an inner diameter and an outer diameter; a metal backing positioned adjacent the inner diameter; and a semiconductor package positioned within the housing and substantially surrounding the half-cylinder piezoelectric transducer and the metal backing.

An eleventh aspect of the disclosure relates to an adjustable implant. The adjustable implant includes: a housing; an adjustable portion moveable relative to the housing upon application of a force supplied by an external adjustment device; a sensor disposed within the housing and configured to measure an angular position of an actuator positioned within the housing; a controller communicatively coupled to the sensor and configured to determine at least one of a distraction force and distraction length based on the angular position of the actuator; and a switch configured to activate at least one of the controller and sensor.

A twelfth aspect of the disclosure relates to a method. The method includes: providing an adjustable implant including: a housing and an adjustable portion moveable relative to the housing upon actuation of an actuator within the housing upon application of a force supplied by an external adjustment device; a sensor configured to sense an angular position of the actuator; and communicatively coupled to the sensor and configured to determine at least one of a distraction force and distraction length based on the angular position of the actuator; and activating at least one of the controller and the sensor when the external adjustment device is within a threshold proximity to the adjustable implant.

A thirteenth aspect of the disclosure relates to an implant configured to be implanted within a patient. The implant includes: a controller; an energy harvesting component configured to harvest energy imparted on the implant during movement of the patient having the implant therein; and an energy storage device configured to store the energy harvested by the energy harvesting component, wherein the energy harvested by the energy harvesting component provides power for the controller.

A fourteenth aspect of the disclosure relates to a method. The method includes: implanting an implant within a patient; harvesting energy from stresses imparted on the implant during movement by the patient having the implant implanted therein; and using the harvested energy to power at least one of a controller and a transducer of the implant.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 12 shows schematics of various techniques for using dual sensors to analyze magnetic fields;

FIG. 13 shows a perspective view of a signal transmission device according to embodiments of the disclosure;

FIG. 14 shows a cross-sectional view of the signal transmission device within the housing of the implant according to embodiments of the disclosure;

FIG. 20 depicts an illustrative computing system according to embodiments of the disclosure.

Figure 1:
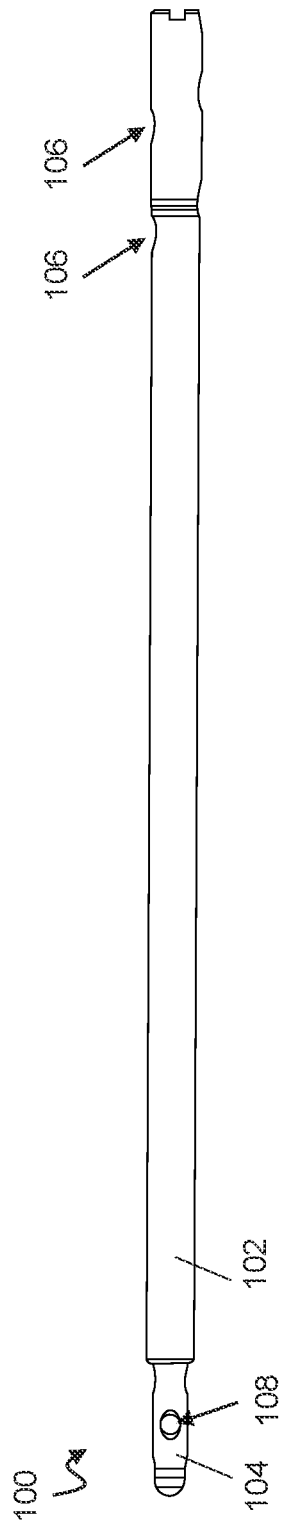
FIG. 1 shows a side view of an adjustable implant according to embodiments of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of an adjustable implant, an adjustable implant system and associated methods. The embodiments described herein can be used as an extramedullary limb lengthening device/system, intramedullary limb lengthening device/system, an adjustable spinal device/system. It is also contemplated that the embodiments described herein can be used in spinal fixation devices/systems, such as for example, in the treatment of scoliosis. More specifically, the present disclosure is directed to an adjustable implant having smart electronics that allows the adjustable implant to work more efficiently and intelligibly.

In certain embodiments, a system is provided for adjusting the position of two bone portions relative to each other that includes: (1) an adjustable implant 100 having various smart components (FIGS. 1-4) fixed within a patient, (2) an external adjustment device 400 (also referred to as an external remote control "ERC") positioned external to the patient (FIGS. 17-19), and (3) an external interface device 305, e.g., a computer, a tablet, a smartphone, one or more Apps, etc., (FIG. 16) for interfacing with smart components in the adjustable implant 100. In alternative embodiments, some or all of the functions provided by external interface device 305 are integrated into external adjustment device 400.

I. General Implant Discussion

FIG. 1 shows a perspective view of the adjustable implant (i.e., distraction/compression device) 100. As shown, the adjustable implant 100 includes a housing 102 and an adjustable portion 104 moveable relative to the housing 102. The adjustable portion 104 may include a distraction rod configured to telescopically move relative to the housing 102. The housing 102 includes at least one fixation aperture 106 configured to receive a bone anchor therein for coupling the housing 102 to a first bone portion. The adjustable portion 104 includes at least one fixation aperture 108 configured to receive a bone anchor therein for coupling the adjustable portion 104 to a second bone portion. Thus, the second bone portion may also move relative to the first bone portion during movement of the adjustable portion 104 relative to the housing 102.

In order to grow or lengthen bone, the bone either has a pre-existing separation or is purposely cut or broken (e.g., via an osteotomy) to create this separation, dividing the bone into a first section and a second section. The cut may be done prior to implanting and securing the implant 100 or may be done after the implant 100 is implanted, for example by use of a flexible Gigli saw. As will be described herein, the adjustable portion 104 is configured to contract and/or retract relative to the housing 102. The implant 100 is configured to allow controlled, precise translation of the adjustable portion 104 relative to the housing 102 by non-invasive remote control, and thus controlled, precise translation of the bone segment that is secured to the adjustable portion 104 relative to the bone segment coupled to the housing 102.

Over the treatment period, the bone is regularly distracted, creating a new separation, into which osteogenesis can occur. Regularly distracted is meant to indicate that distraction occurs on a regular or periodic basis which may be on the order of every day or every few days. An exemplary distraction rate is one millimeter per day, although, other distraction rates may be employed. That is to say, a typical distraction regimen may include a daily increase in the length of the implant 100 by about one millimeter. This may be done, for example, by four lengthening periods per day, each having 0.25 mm of lengthening. The implant 100, as disclosed in more detail below, has a magnetic drive system, which allows the adjustable portion 104 to be telescopically extended from the housing 102, thus forcing the first section and the second section of the bone apart from one another. The implant 100 can also be regular compressed for controlled fusion of bone.

Figure 2:
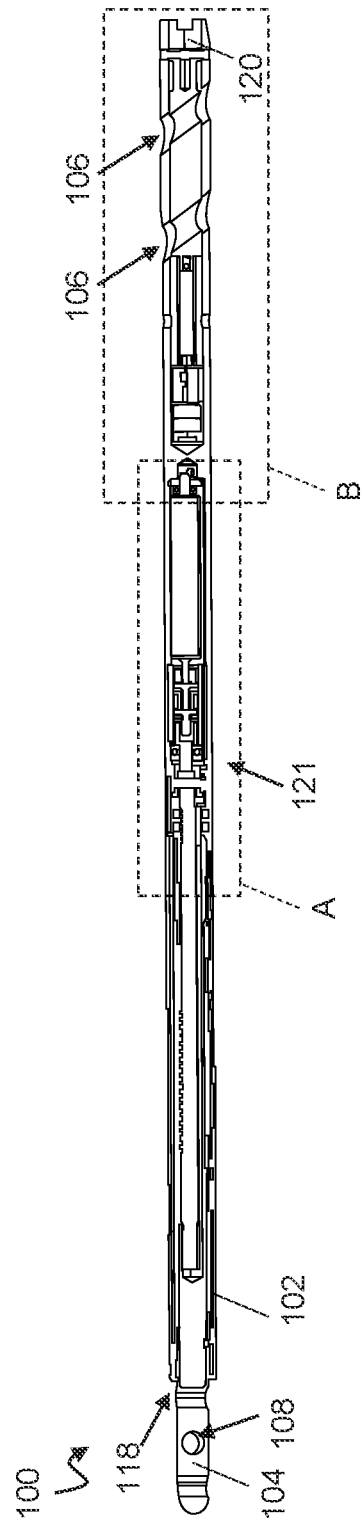
FIG. 2 shows a cross-sectional view of an adjustable implant according to FIG. 1.
Figure 3:
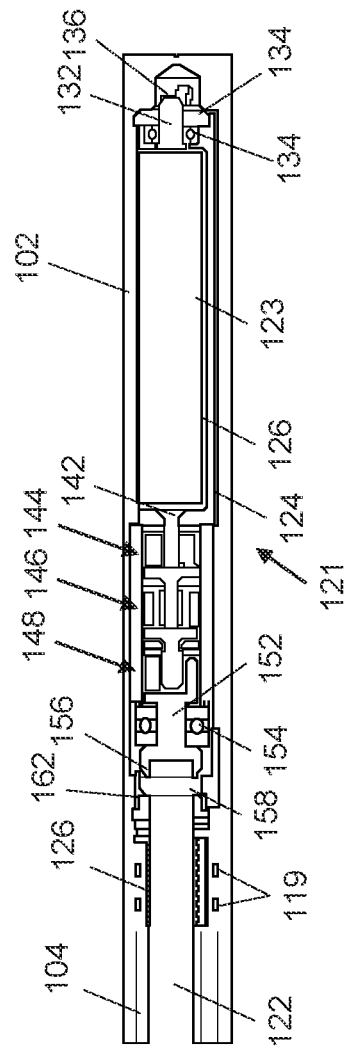
FIG. 3 shows an enlarged cross-sectional view of the actuating components of the adjustable implant at region A.
Figure 4:
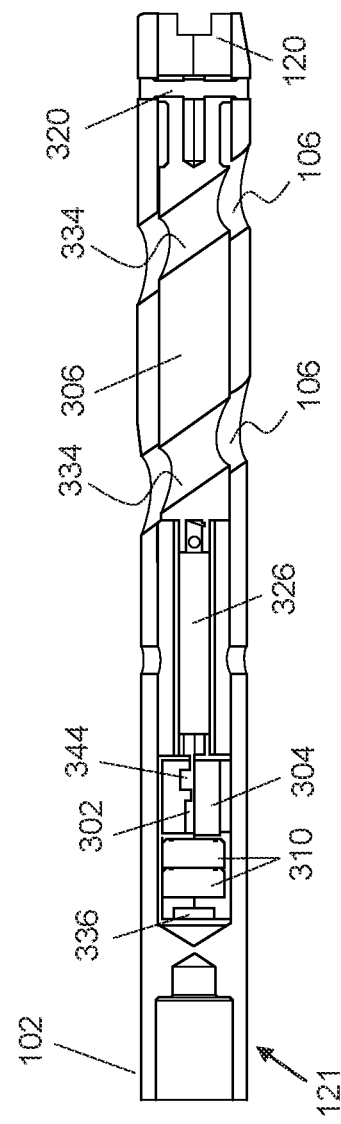
FIG. 4 shows an enlarged cross-sectional view of the adjustable implant at region B.

FIG. 2 depicts a cross-sectional view of the implant 100 shown in FIG. 1, which shows at one end, the housing 102 has an opening 118 for receiving the adjustable portion 104. FIG. 2 also highlights two sections A and B, which are depicted in greater detail in FIGS. 3 and 4 respectively. FIG. 3 generally depicts an enlarged cross-sectional view of the actuating components of the implant 100 and FIG. 4 depicts an enlarged cross-sectional view of various "smart components" of the implant 100.

As shown in FIG. 3, one or more o-rings 119 can be positioned about the adjustable portion 104 between the adjustable portion 104 and the housing 102. In some embodiments, a portion of the outer surface of the adjustable portion 104 and/or a portion of an internal surface of the housing 102 can be recessed to accommodate the o-ring(s) 119. The o-ring(s) 119 can help facilitate proper sealing between the housing 102 and the adjustable portion 104 so that bodily fluid does not enter the housing 102 when the implant 100 is implanted. The housing 102 is sealably closed at the other end by the attachment of an end cap 120. The end cap 120 may be attached to the housing 102 by means of welding, adhesive bonding, or other joining techniques. Further, an o-ring (not shown) may be provided between the end cap 120 and the housing 102 to help provide a seal. In use, the adjustable portion 104 is driven from the housing 102 by means of an actuator 121. The actuator may include a lead screw 122 and a cylindrical permanent magnet 123. The lead screw 122 turns inside a nut 126 that is secured to an inner surface adjacent to a cavity of the adjustable portion 104 in which the lead screw 122 is disposed. The nut 126 is positioned between the lead screw 122 and the adjustable portion 104. The lead screw 122 is mechanically coupled, in an indirect manner, to the cylindrical permanent magnet 123 contained within a magnet housing 124. As explained in more detail herein, rotation of the cylindrical permanent magnet 123, which is magnetically driven by an external adjustment device 400 (FIGS. 17-19), effectuates rotation of the lead screw 122. Rotation of the lead screw 122 then translates into axial movement of the adjustable portion 104 relative to the housing 102.

The cylindrical permanent magnet 123 is fixedly contained within a magnet casing 126 using, for example, an adhesive such as an epoxy. The magnet casing 126 rotates relative to the magnet housing 124. The cylindrical magnet 123 may be a rare earth magnet such as Nd—Fe—B and may be coated with Parylene or other protective coatings in addition to being protected within the magnet casing 126, for example hermetically potted with epoxy. The magnet casing 126 contains an axle 132 on one end which attaches to the interior of a radial bearing 134. This arrangement allows the cylindrical magnet 134 to rotate with minimal torsional resistance. A maintenance member 136 may be positioned in proximity to and/or adjacent to the cylindrical permanent magnet 123. The maintenance member 136 keeps the implant 100 from being accidentally adjusted by movements of the patient. The maintenance member 136 is positioned proximate and axially spaced from the magnet 123. The maintenance member 136 is made from a magnetically permeable material, such as 400 series stainless steel. The maintenance member 136 can, for example, be generally cylindrical in shape having two spaced apart tabs separated by gaps. When the implant 100 is not being adjusted (e.g., using an external adjustment device), the magnetic poles of the radially-poled cylindrical magnet are magnetically attracted to the tabs. However, when the magnet 123 is forced to rotate due to the effect of a sufficiently large rotating magnetic field, the magnet 123 overcomes the smaller attractions of the tabs. The maintenance member 136 also includes flanged extension and/or flanged extension fingers for engaging with the end cap 120 and/or housing 102. Additional details of the maintenance member can be found in U.S. Pat. Pub. 20190015138, filed Jul. 26, 2018, which is incorporated herein by reference as if set forth in its entirety. Other maintenance members such as those disclosed in U.S. Pat. No. 8,734,488 filed Aug. 4, 2011 and U.S. application Ser. No. 13/525,058 filed Jun. 15, 2012 can also be used, each of which are incorporated herein by reference as if set forth in its entirety.

At its other, opposing end, the magnet housing 126 includes an axle 142, which is attached to a first planetary gear set 144. The axle 142 includes the sun gear of the first planetary gear set 144, the sun gear turning the planetary gears of the first planetary gear set 144. The first planetary gear set 144 serves to reduce the rotational speed and increase the resultant torque delivery from the cylindrical magnet 123 to the lead screw 122. A second planetary gear set 146 and a third planetary gear set 148 are also shown between the first planetary gear set 144 and the lead screw 136, for further speed reduction and torque augmentation. The number of planetary gear sets and/or the number of teeth in the gears may be adjusted, in order to achieve the desired speed and torque delivery.

The planetary gear sets 144, 146, 148 output to a planetary gear output shaft 152. The planetary gear output shaft 152 extends through a thrust bearing 154 and is secured (by welding and the like) to a lead screw coupling cap 156. The lead screw 122 is secured to the lead screw coupling cap 156 by a locking pin 158, which extends through a hole in the lead screw 122 and holes in the lead screw coupling cap 156. A locking pin retainer 162 is a cylinder that surrounds the locking pin 158, holding this assembly together. Attaching the lead screw 122 to the rest of the magnet/gear assembly in this manner, assures that the design is not over-constrained, and thus that the lead screw 122 does not gall with the nut 126. In addition, a biocompatible grease and/or fluorinated oil, such as, for example Krytox® (Krytox is a registered trademark of E. I. DU PONT DE NEMOURS AND COMPANY), may be used on the moving parts (lead screw, nut, bearings, housing, and distraction shaft) in order to minimize frictional losses. The lead screw 122 is able to freely rotate within a cavity of the distraction shaft 104, and only need engage with the short length of the nut 126, this feature also minimizing frictional losses.

II. Smart Components

In certain embodiments, one or more smart components are described that enhance the operation of the implant 100. As shown in FIG. 4, the various smart components can be positioned within a chamber in the housing 102 that is separate from the actuating components (i.e., the actuator 121).

At the core of these enhancements is a controller 302 that provides, e.g., data processing and storage operations, and may be any type of controller known and used in the art including: high performance microcontrollers (MCUs), Programmable System on Chip (PSoC), Application Specific Integrated Circuit (ASIC) or any other type of controller or microcomputer. The controller 302 may be disposed on a printed circuit board which may also contain other electronic circuitry and connect other electrical components including: Analog to Digital Converter (ADC), Digital to Analog Converter (DAC), op-amps, memory, or any other electrical component. The controller 302 may further include a frequency synthesizer (i.e., creates carrier waves for the transceiver), power amplifiers, noise filters (i.e., conditions carrier wave), power and read strain gauges (i.e., force sensor controls), and may be configured to adjust carrier waves, power, etc., such as by computer executable instructions that interface with a user via a graphical user interface, as discussed below.

In addition, in certain embodiments, a transducer 304 coupled to the controller 302 provides a communication platform to exchange data with an external interface device 305 (FIG. 16) using, e.g., ultrasonic or ultrasound communications. In certain embodiments, the communication platform may include any device that induces sound waves or a mechanical vibration, and converts soundwaves to electronic signals, including for example: a piezoelectric transducer, a single crystal ultrasonic transducer, a lead zirconate titanate (PZT) ultrasonic transducer, piezoelectric polyvinylidene fluoride (PVDF) ultrasonic transducer, capacitive micromachined ultrasonic transducers (CMUT), piezoelectric micromachined ultrasonic transducers (PMUT), or any ultrasonic transducer known and used in the art. In some embodiments, the ultrasonic transducer may include one or more of: a thin film ultrasonic transducer, a flat ultrasonic transducer, a tubular ultrasonic transducer, a half-tubular ultrasonic transducer, etc. A benefit, for example, of a thin film ultrasonic transducer is the reduced thickness of the ultrasonic transducer. A benefit, for example, of a flat ultrasonic transducer is improved transmission and reception characteristics. A benefit, for example, of a tubular ultrasonic transducer is multi-directional (360° radial directional) transmission and reception. The type of ultrasonic transducer may be chosen to complement the application of the adjustable implant 100. In another embodiment, the transducer 304 can include a radiofrequency transducer. The transducer 304 is configured to receive instructions and data from the controller and configured to send such instructions and data to an external adjustment device 400 (FIGS. 17-19) and/or an external interface device 305, via, for example, ultrasound or radiofrequency waves. The transducer 304 is also configured to receive data and/or treatment instructions from the external interface device 305 or external adjustment device 400. It is understood that while various embodiments described herein utilize an ultrasonic device for a communication platform, any wireless device or technology could likewise be utilized, e.g., radio, Bluetooth, etc.

In order to power the smart components of the implant 100, one or more power supply components 310 may be used. The power supply components 310 include at least one battery energy storage device. For example, at least one lithium-ion battery or silver oxide battery could be used. However, any other now known or later developed medical grade energy storage device could be used without departing from aspects of the disclosure.

Further details of various smart components are provided below. It is understood that an implant may include one or more of the following components.

A. Load Cell

Figure 5:
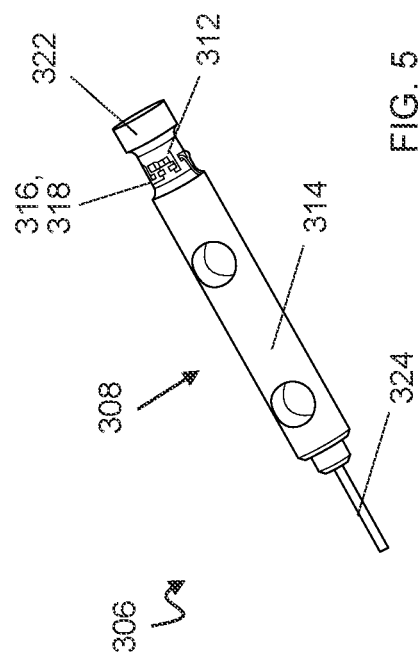
FIG. 5 shows a perspective view of the load cell of the adjustable implant according to embodiments of the disclosure.
Figure 8:
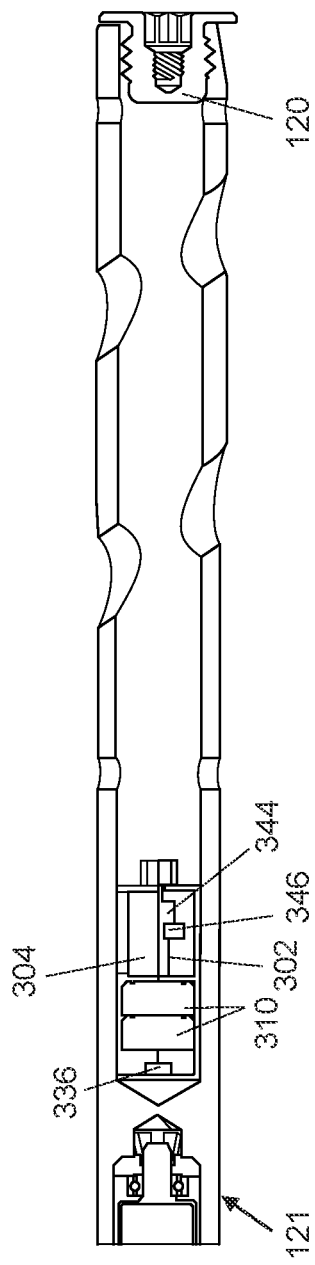
FIG. 8 shows an enlarged cross-sectional view of an alternative embodiment of the adjustable implant at region B without the load cell.

Referring to FIGS. 4 and 5, the load cell 306 is positioned within the housing 102 and is configured to measure a linear load, i.e., force, imparted on the adjustable implant 100. Illustrative types of loads that can be measured include "bone loading" and "elongation distraction." Bone loading measures the amount of stress on the bone resulting from weight bearing activities, e.g., standing, walking, lifting, etc. Elongation distraction (or contraction) refers to the amount of stress imparted on the bone when the implant 100 is being adjusted, i.e., during movement of the adjustable portion 104 relative to the housing 102.

As shown in FIG. 4, both the housing 102 and load cell 306 include one or more apertures 106, 334, respectively, for receiving bone anchors therein (not shown). The apertures 334 of the load cell 306 have a smaller diameter than the apertures 106 within the housing 102 to allow the bone anchors to primarily anchor to the load cell 306, as opposed to the housing 102. This arrangement accordingly allows the load cell 306 to slide within the housing when a linear force is applied. The load may for example result from an adjustment of the implant (i.e., the adjustable portion 104 relative to the housing 102) or from a bone loading activity in which a force is applied to the load cell via bone anchors (e.g., bone relative to the housing 102). The linear motion of the load cell 306 then allows the load imparted on the bone or adjustable implant 100 to be detected by the load cell 306. In the example shown, the two apertures are shown angled within the implant 100. However, it is understood that other arrangements could be utilized, e.g., one, three or four perpendicular apertures, etc.

The load cell 306 includes at least one sensor, such as for example, a strain gauge. As shown in FIG. 5, the load cell 306 includes a substantially tubular body 308 having a first portion 312 with an outer diameter that is smaller than an outer diameter of the remaining portion 314 of the tubular body 308. In certain embodiments, the load cell comprises a force transducer that converts a force into an electrical signal. As the force applied to the load cell increases, the electrical signal changes proportionally, e.g., based on a change in electrical resistance. As shown, the first portion 312 of the load cell 306 includes a strain gauge having a first sensing element 316 and a second sensing element 318 that, e.g., are configured in a Wheatstone bridge arrangement to generate a voltage output that measures a displacement, e.g., in the range of 0-10 mm. Accordingly, as linear stress is imparted to the bone and/or implant 100, the load cell 306 can generate a voltage that is converted into a load value by the controller 302.

In some embodiments, the load cell 306 is coupled within the housing 102 via pin 320 (FIG. 4) extending through a pin hole 322 (FIG. 5) within the load cell 306 at a first end. However, other means for coupling the load cell 306 to the housing 102 can also be used without departing from aspects of the disclosure, such as for example a retainer member such as the one disclosed in U.S. 63/053,036 filed on Jul. 17, 2020, which is incorporated by reference as if set forth in its entirety.

Opposite the first end, the load cell 306 can be coupled to the controller 302 via wiring 324. In some embodiment, a protective housing (e.g., composed of a polymer such as polyether ether ketone (PEEK)) 326 can be positioned adjacent the load cell 306 within the housing 102. The protective housing 326 substantially surrounds the wiring 324 from the load cell 306 to the controller 302 within the housing 326 and protects the wiring 324 within housing 102.

Figure 7:
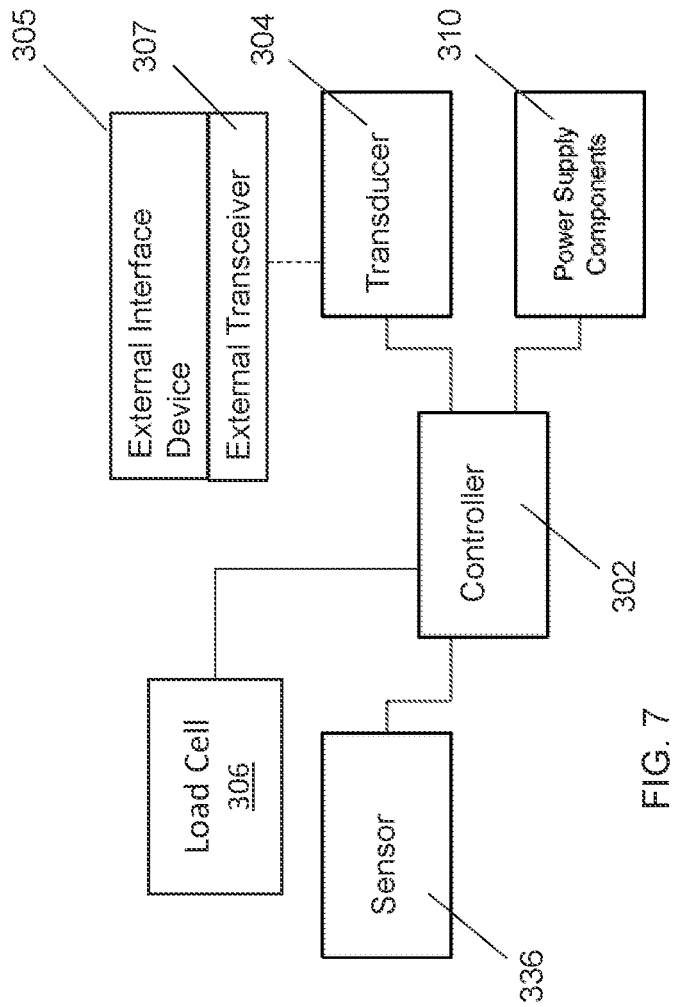
FIG. 7 shows a schematic of the sensor, controller, transducer, and power supply components according to embodiments of the disclosure.

As shown in FIG. 7, the controller 302 is configured to receive electrical signals from the load cell 306 via the wiring 324 and calculate load characteristics, e.g., a distraction force and/or distraction length. In addition, the arrangement can be configured to determine a compression force, and/or compression length based on the load measured by the load cell 306 when the implant 100 is used as a compression device. The controller 302 is configured to digitize the data obtained by the load cell 306, process the data and modulate the data into an ultrasound signal to be communicated by the transducer 304 to an external interface device 305 via a transceiver 307. The external interface device 305 and the transceiver 307 are each positioned external to the patient.

An illustrative method involving a load cell 306 includes implanting the implant 100 within a patient, such as for example within an intramedullary canal of a bone. An osteotomy is performed to create a first bone portion and a second bone portion. The housing 102 is coupled to the first bone portion and the adjustable portion 104 is coupled to the second bone portion. The method also includes adjusting the implant 100 having the housing 102, an adjustable portion/rod 104 moveable relative to the housing and a load cell 306 within the housing 102 for measuring a load imparted on the implant 100 during movement of the adjustable portion 104 relative to the housing 102. The method also includes measuring the load imparted on the implant 100 during movement of the adjustable portion 104 relative to the housing 102. More specifically, the measuring of the load includes using the load cell 306 to measure the load imparted on the bone anchors (not shown) positioned within the apertures 106 of the housing 102 and the apertures 334 of the load cell. The method can also include sending the measured load to an external interface device 305 via the transducer 304 and a transceiver 307. A medical professional can then view the measured load data from the external interface device 305 and use the measure load to determine additional data, such as for example, a distraction force, distraction torque and a distraction length or a compression force, compression torque and a compression length. The medical professional can then determine treatment instructions based on such data. The implant 100 and/or external adjustment device 400 can receive the treatment instructions and adjust the implant 100 based on the treatment instructions.

B. Actuator Position Sensing

Figure 6:
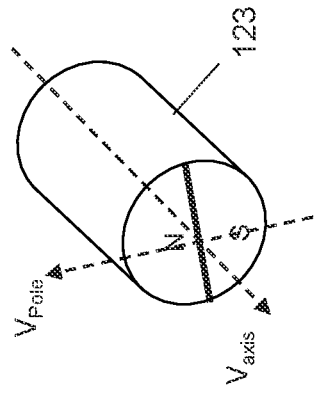
FIG. 6 shows a perspective view of the magnet of the actuator of the implant.

Position sensing may be provided to determine a position of the actuator 121, e.g., how far it has been distracted or compressed, by measuring and tracking angular (i.e., rotational) movements of the actuator 121. To achieve this, a sensor 336 such as that shown in FIG. 4 can be utilized to monitor an angular position of the actuator 121 of the adjustable implant 100. More specifically, the sensor 336 is configured to monitor an angular position of the magnet 123 of the actuator 121 (FIG. 3), for example, by measuring at least one of a magnetic field strength, polarity, and dynamic direction. For example, as shown in FIG. 6 the sensor 336 monitors a position of the dipole moment or vector $V_{Pole}$ representing the direction of the magnetic field of the magnet 123 of the actuator 121 as it rotates about the axis extending longitudinally through the magnet, $V_{axis}$ representing possible angles of 0°-360°.

In one embodiment, the sensor 336 can include a hall effect sensor, and more specifically, a unidirectional hall effect sensor, e.g., implemented on a printed circuit board. The sensor 336 can also include a rotary hall effect sensor, which can include, for example, a 4-hall element arrangement. The sensor 336 is positioned adjacent to and/or in proximity to the actuator 121. More specifically, the sensor 336 is positioned such that the sensor 336 can monitor the magnetic field emanating from the magnet 123 of the actuator 121 and collect angular position data. For example, in one embodiment, at each full rotation, sensor 336 can output a predefined signal. In other embodiments, sensor 336 can output a predefined signal at partial rotations, e.g., each quarter rotation as determined by a 4-hall element arrangement.

As shown in the illustrative system diagram of FIG. 7, the sensor 336 is communicatively coupled to the controller 302 (e.g., via wiring) and the controller 302 is configured to receive the angular position data of the actuator 121 from the sensor 336. In one embodiment, the controller 302 is configured to calculate and/or determine a distraction length or compression length of the adjustable implant 100 based on the number of rotations (or partial rotations) of the actuator 121. More specifically, the number of rotations of the actuator 121 can be correlated (e.g., with a lookup table) to a number of rotations of the lead screw 122 (FIG. 3) which is then used to determine the overall distraction length or compression length of the implant 100. In alternative embodiments, the collected rotation data can simply be digitized packaged for transmission to an external interface device 305, which can calculate a distraction or compression length.

In certain embodiment, the controller 302 is communicatively coupled to the transducer 304 (e.g., via wiring) and is configured to send data such as the number of rotations to external interface device 305 to be viewed by a medical professional and/or the patient. More specifically, a transceiver 307 positioned external the patient can be used to demodulate the signal transmitted by the transducer 304 into meaningful data digestible and interpretable by the external interface device 305. Once the signal is demodulated, the external transceiver 307 can send the demodulated data to the external interface device 305.

An illustrative method involving actuator position sensing includes implanting the implant 100 within a patient, such as for example within an intramedullary canal of a bone. An osteotomy is performed to create a first bone portion and a second bone portion. The housing 102 is coupled to the first bone portion and the adjustable portion 104 is coupled to the second bone portion. The method also includes adjusting the implant 100 having the housing 102, the adjustable portion/rod 104 moveable relative to the housing 102, an actuator 121 positioned within the housing 102 and configured to cause movement of the adjustable portion 104 relative to the housing 102; and a sensor 336 positioned adjacent to the actuator 121 and configured to monitor an angular position of the actuator 121 of the implant 100. The method also includes sensing, via the sensor 336, an angular position of the actuator 121, or more specifically, the magnet 123 of the actuator 121. The angular position of the magnet 123 can be used to determine a number of rotations of the magnet 123. The method also includes calculating a distraction length or compression length of the implant 100 based upon a number of rotations of the magnet 123/actuator 121. More specifically, the controller 302 positioned within the housing 102 and communicatively coupled to the sensor 336 is configured to determine the distraction length or the compression length of the implant 100. At least one of the distraction length, compression length or the number of rotations of the actuator 121 can be sent to an external interface device 305 via the transducer 304 which is also positioned within the housing 102 and the transceiver 307 positioned external to the patient. A medical professional can then view the determined distraction length and/or number of rotations of the actuator 121 via the external interface device 305. The medical professional can then determine treatment instructions based on such data. The implant 100 and/or external adjustment device 400 can receive the treatment instructions and adjust the implant 100 based on the treatment instructions.

C. Dual Magnet Load Sensors

1. Implant and External Magnet Sensing

Figure 17:
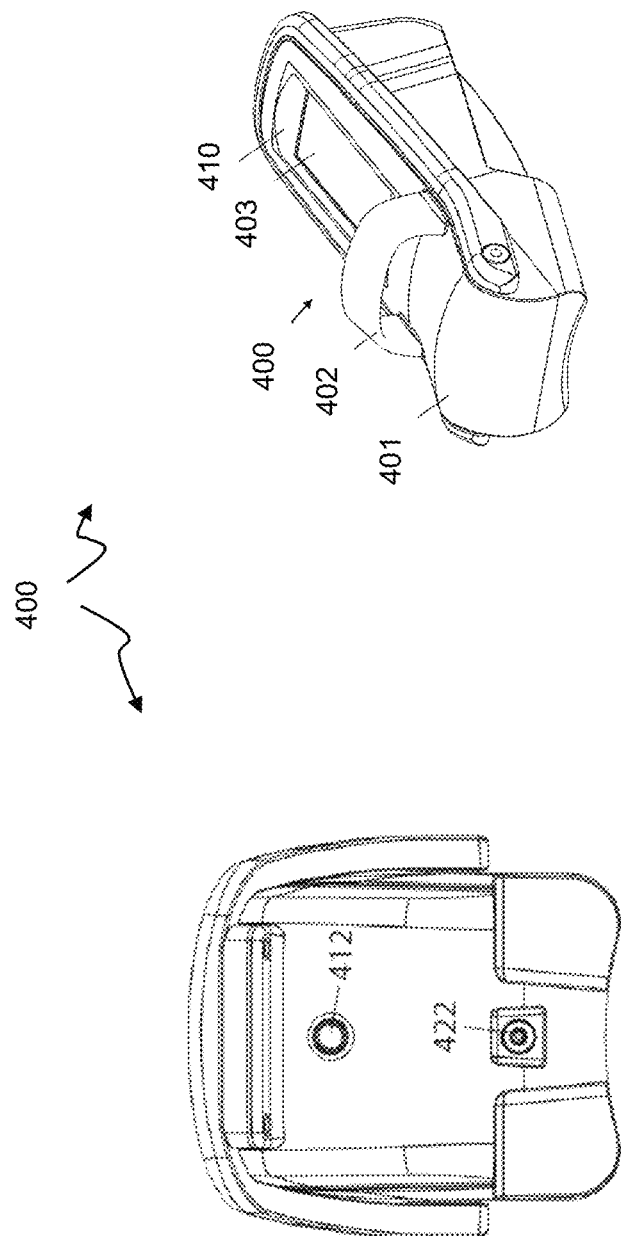
FIG. 17 shows a front view of an external adjustment device according to embodiments of the disclosure.
Figure 18:
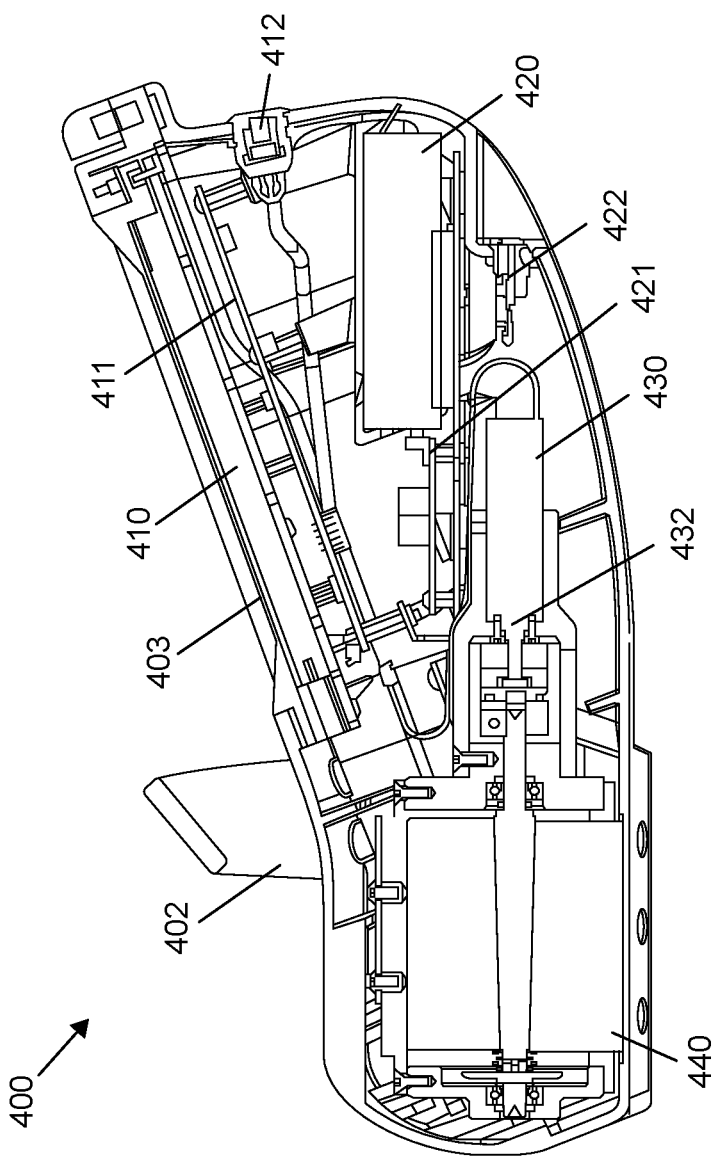
FIG. 18 shows a cross-sectional side view the external adjustment device according to embodiments of the disclosure.
Figure 19:
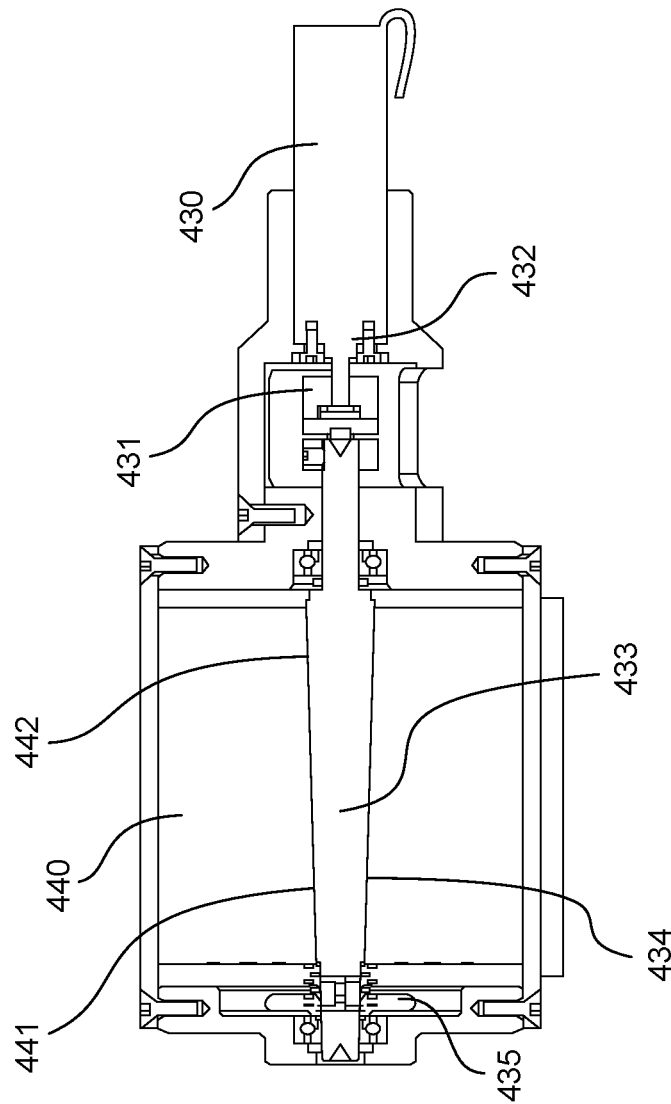
FIG. 19 shows a cross-sectional view of a magnet drive system including a motor having an internal motor speed sensor.

In a further embodiment, in place of or in addition to using a load cell 306 to measure a compression/distraction force, a dual sensor arrangement as described in FIGS. 8-12 may be implemented to measure force loads associated with the adjustable implant 100. In the illustrative embodiment of FIG. 8, a first sensor 336 is included that is configured to measure a position and/or magnetic field information of the actuator 121 of the adjustable implant 100 (e.g., as described herein with reference to the actuator position sensing system) and a second sensor 346 is included in the implant 100 that is configured to measure a position and/or magnetic field information of the external actuator magnet 440 of the external adjustment device 400 (FIGS. 17-19). The moments of the two associated magnets are then evaluated with an algorithm to determine, e.g., a torque and/or compression/distraction force.

The first sensor 336 and second sensor 346 each include, for example, a printed circuit board having at least one sensor such as, for example, a hall effect sensor, configured to measure at least one of a magnetic field strength, polarity, and dynamic direction. In one example, the first sensor 336 includes a unidirectional hall effect sensor to read the position of the internal actuator magnet 123 and the second sensor 346 includes an omnidirectional hall effect sensor to read the position of the magnet of the external actuator 440 of the external adjustment device 400.

The first sensor 336 can be positioned adjacent to and/or in proximity to the actuator 121 and may comprise a multiple hall effect sensor configured to make differential strength measurements. In one embodiment, the first sensor 336 can include a rotary hall effect sensor (e.g., a four-hall effect sensor) and the second sensor 346 configure to measure magnetic strength in three axis. The second sensor 346 can be positioned at a location where the external magnet and internal magnet are least coupled, e.g., on an opposite side of the controller 302 from the first sensor 336 such that the controller 302 is positioned between the first 336 and second sensors 346. The controller 302 is configured to determine a position of the first actuator 336 and the second actuator 440 relative to each other at a given time based on data from obtained by the first and second sensors 336, 346. More particularly, the controller 302 is configured to monitor a position of the rotating magnet 123 (FIG. 3) of the actuator 121 and a position of the at least one rotating permanent magnet of the external actuator 440 in the external adjustment device 400.

Figure 10:
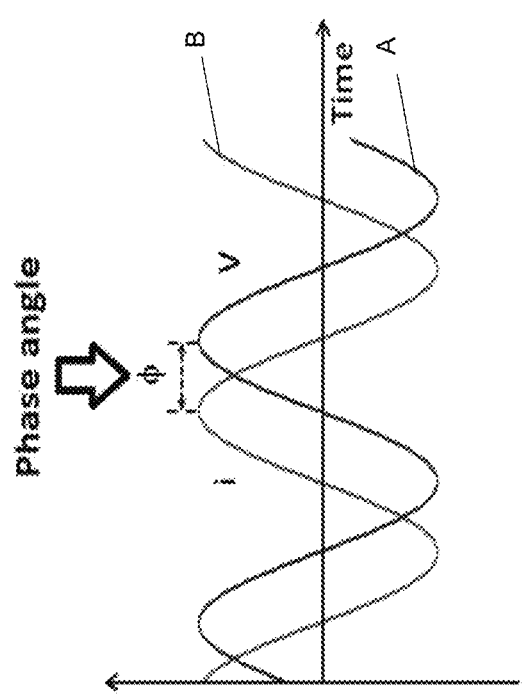
FIG. 10 shows a phase shift diagram of the relationship of the magnet of the implant and the magnet of the external adjustment device.

FIG. 10 shows a phase shift diagram with line A representing the phase shift of the magnet of external actuator 440 of the external adjustment device 400 and line B representing the phase shift of the magnet 123 of the implant 100. As shown, the magnet 123 may lag behind the actuator 440 due at least in part to the torque put on the magnet 123 from the gear assembly (planetary gears 144, 146, 148) and the lead screw 122 interacting with the adjustable portion 104 such that a phase angle can be determined. By analyzing the lag/phase angle, coupling states, stalling states, force measurements, non-union states, consolidation states, etc., can be determined. For example, if line B lags too far behind line A, a stalling condition may have occurred.

Figure 11:
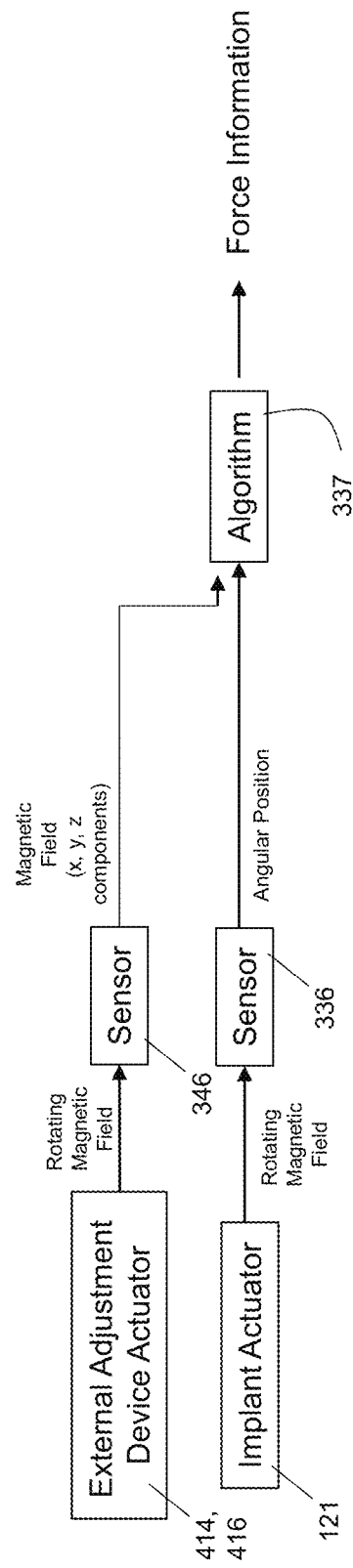
FIG. 11 shows a schematic of a system used to determine the distraction force/torque by the adjustable implant of FIG. 8 according to one embodiment.

FIG. 11 shows an illustrative schematic of how the distraction force or distraction torque, or the compression force or compression torque can be calculated. In one embodiment, the sensor 336 monitors the rotating magnetic field from the implant actuator 121 and provides an angular position of the magnet 123. The sensor 346 monitors the rotating magnetic field of the actuator 440 of the external adjustment device 400 and, e.g., provides the x, y, and z components, yaw, pitch and roll of the magnetic field. An algorithm 337 can be used to process the angular position of the rotating magnet 440 of the external adjustment device 400 and/or a distance of the rotating magnet 440 from the sensor 346 and determines one or more forces (e.g., a distraction force and distraction torque, and/or compression force and compression torque) based on the angular position of the implant magnet 123 and the angular position of the rotating magnet 440. In some embodiments, the algorithm 337 calculates one or more forces by applying one or more functions or lookup tables to readings from the sensors 336, 346. In some examples, readings from the sensors 336, 346 are provided as input to a machine learning algorithm trained on angular position and/or magnetic field data to output force information.

Figure 9:
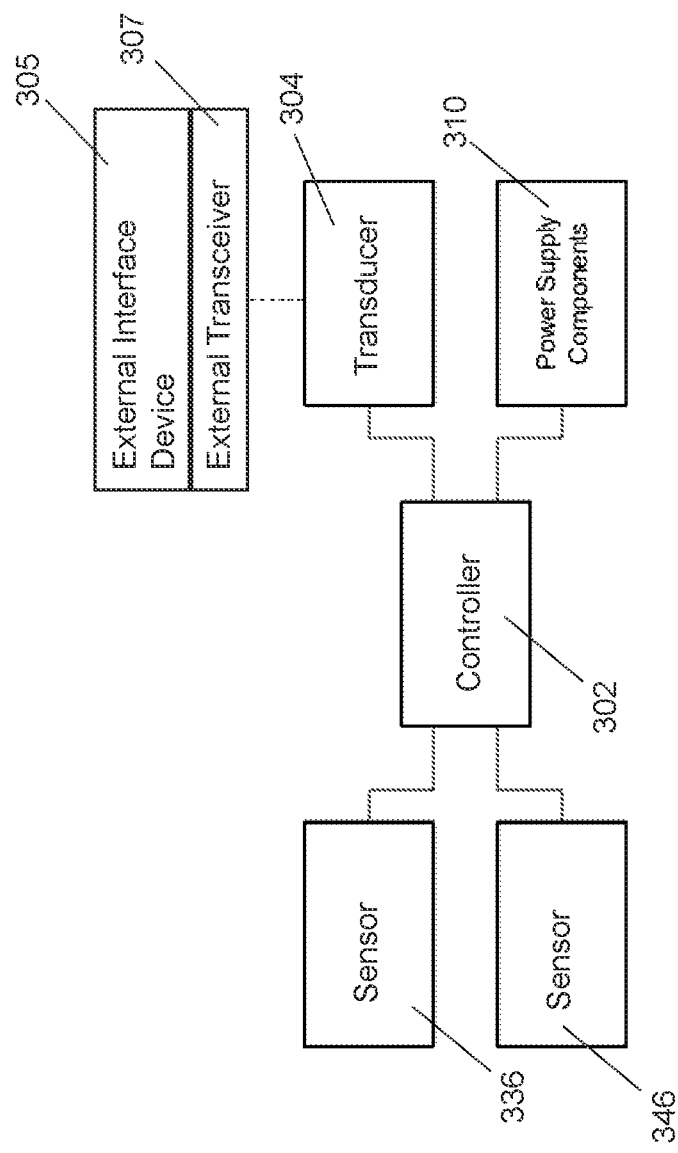
FIG. 9 shows a schematic of the first sensor, second sensor, controller, transducer, and power supply components according to embodiments of the disclosure.

FIG. 9 depicts an associated system diagram in which the controller 302 captures and processes data from sensors 336, 346. Once processed, the transducer 304 is configured to send data associated with the first sensor 336 and the second sensor 346 to an external interface device 305 to be viewed by a medical professional and/or a patient. More specifically, an external transceiver 307 positioned external the patient can be used to demodulate the signal transmitted by the transducer 304 into meaningful data digestible and interpretable by the external interface device 305. Once the signal is demodulated, the transceiver 307 can send the demodulated data to the external interface device 305. Depending on the implementation, either controller 302 or an external system can implement algorithms to compute the force information from measurements captured by sensors 336, 346. In some examples, an algorithm calculates the distraction/compression force/torque by applying one or more functions or lookup tables to the measurements captured by the sensor 336, 346. In some embodiments, the measurements are provided as input to a machine learning algorithm trained on distraction force/torque data and the distraction force/torque is provided as output.

The top half of FIG. 12 describes the relationship between the implant magnet 123 and the external (ERC) magnet. As shown on the left, the external magnet and implant magnet are coupled. In the middle, when the ERC magnet tilts, the implant magnet follows immediately indicating the two are in phase with no torque. On the right, the implant magnet tilt lags behind the ERC magnet, indicating a counter torque.

An illustrative method involving a dual sensor arrangement includes implanting the implant 100 within a patient, such as for example within an intramedullary canal of a bone. An osteotomy is performed to create a first bone portion and a second bone portion. The housing 102 is coupled to the first bone portion and the adjustable portion 104 is coupled to the second bone portion. The implant 100 having the housing 102 and the adjustable portion 104 moveable relative to the housing 102 is adjusted. A position of the actuator 121 configured to cause movement of the adjustable portion 104 relative to the housing 102 is measured via the sensor 336. A position of the actuator 414, 416 of an external adjustment device 400 configured to actuate the actuator 121 of the implant 100 is measured via the sensor 346. At least one of a distraction force a distraction torque, a compression force, and compression torque is determined based on a position of the actuator 121 and a position of the actuator 414, 416. As discussed herein, the sensor 336 includes a unidirectional hall effect sensor and the sensor 346 includes an omnidirectional hall effect sensor. The controller 302 is positioned between the sensors 336, 346 and determines at least one of a distraction force, a distraction torque, compression force, and compression torque. at least one of the distraction force, distraction torque, compression force, and compression torque is sent via the transducer 304 to an external interface device 305 and via the transceiver 307 (FIGS. 7 and 9). A medical professional can then view the determined distraction force, distraction torque, compression force, and/or compression torque via the external interface device. The medical professional can then determine treatment instructions based on such data. The implant 100 and/or external adjustment device 400 can receive the treatment instructions and adjust the implant 100 based on the treatment instructions.

2. Dual Implant-Magnet Sensing

In an alternative embodiment for measuring loads within the implant 100, dual multi-dimensional sensors 341, 343 are utilized to obtain two separate magnetic field readings associated with the implant's magnet 123 relative to the external magnet 440 of the external adjustment device 400, as shown in the bottom half of FIG. 12. Unlike the prior arrangement, this arrangement determines one or more associated forces independently of the position of the external adjustment device 400. Instead, the two sensors 341, 343 are strategically located at different positions in the housing to read the magnetic field (i.e., field vectors) of the implant magnet 123 relative to the external magnet 440 of the external adjustment device 400, e.g., as the external magnet interacts with the implant magnet 123. The sensed magnetic field results can then be evaluated by the controller 102 to determine load values (i.e., forces). Multi-dimensional sensors 341, 343 may for example include three-dimensional or multi-axis hall effect sensors configured to read field vectors in multiple dimensions.

This approach is further described with reference to the bottom half of FIG. 12. When the moment of the implant magnet 123 follows that of the external magnet, the magnetic field vectors or lines are the same. However, when the moment of the implant magnet 123 lags the moment of the external magnet 440, the vectors 345 near the implant magnet will lag behind the vectors 347 farther from the implant magnet 123. That is, magnetic field lines are parallel to the axes of the implant when the two moments are pointing in the same direction. However, when the moment of the implant magnet lags, the field lines would look helical or skewed as shown. The rotation of the moment may be described with the formula:

$$\text{Theta}=\text{tangent}(\text{magnitude of } x/\text{magnitude of } y).$$

In certain embodiments, the moment 347 of the sensor 343 further away from the implant magnet 123 is used as the reference, and when the sensor 341 closer to the implant magnet observes a lag, the angle is subtracted from the reference. The lag is, e.g., caused by a counter-torque, which is directly proportional to the counter-force, which is the resisting force against the soft tissues when the implant 100 is distracted.

To correlate the angular lag to a linear force, the linear force can be calibrated by a test instrument, e.g., an ERC fixture, which is instrumented with a force gauge that can constrain the two ends of the implant 100. When the implant 100 is extended by the ERC, the linear force is recorded. The same approach can monitor stalling and coupling/decoupling between two magnets and can locate the moving external magnet in space.

D. Half-Cylinder Piezo Signal Transmission

Turning to FIGS. 13-14, in yet another embodiment, the described transducer 304 may include a signal transmission device 500 that includes a half-cylinder piezoelectric transducer 502 for communicating data. Like transducer 304 of FIGS. 4 and 7, the signal transmission device 500 is configured to transmit data associated with the adjustable implant 100 to an external adjustment device 400 or an external interface device 305, e.g., to be viewed by a medical professional and/or a patient. For example, a transceiver 307 (FIG. 7) positioned external the patient can be used to demodulate the signal transmitted by the signal transmission device 500 into meaningful data digestible and interpretable, e.g., by the external interface device 305. Once the signal is demodulated, the transceiver 307 can send the demodulated data to the external interface device 305.

The signal transmission device 500 is configured to transmit a directional signal relative to the patient having the adjustable implant 100 implanted therein. As shown in FIGS. 13 and 14, the signal transmission device 500 may include a half-cylinder piezoelectric transducer 502 positioned within a package 504 that is positioned within the housing 102. Housing 102 may comprise any metallic housing. In one embodiment, the housing 102 can include a titanium housing. In another embodiment, the housing 102 can include non-ferrous, biocompatible metal such as, for example, a Biodur® (Biodur is a registered trademark of CRS HOLDINGS, INC.) housing. As shown, the half-cylinder piezoelectric transducer 502 includes an inner diameter 506 (FIG. 14) and an outer diameter 508 (FIG. 14). A metal backing 510 is positioned adjacent the inner diameter 506. The metal backing 510 can include, for example, a stainless steel. The metal backing 510 may be a half-cylinder metal backing. Disposed between the half piezoelectric transducer 502 and the metal backing 510 is a filler 511 (FIG. 14), which can include any viscous material that closely matches the acoustic impedance of the piezoelectric transducer and housing including, e.g., water, mineral oil, acoustic gel, etc. In an illustrative embodiment, the filler 511 can include, e.g., at least one of: a bio-compatible epoxy, fluorinated oil such as Krytox® (Krytox is a registered trademark of E. I. DU PONT DE NEMOURS AND COMPANY), and silicon oil. The package 512 is positioned within the housing 102 and substantially surrounding the half-cylinder piezoelectric transducer 502 and the metal backing 510. As shown, the package 504 is positioned adjacent the outer diameter of 508 of the half-cylinder piezoelectric transducer 502. Disposed between the half piezoelectric transducer 502 and the semiconductor package 504 is a filler 513. The package 504 can also house the power supply components 310. The filler 513 can include at least one of: a super epoxy, fluorinated oil such as Krytox® (Krytox is a registered trademark of E. I. DU PONT DE NEMOURS AND COMPANY), and silicon oil. The half-cylinder piezoelectric transducer 502 can be a 1 KHz-10 MHz piezoelectric transducer, e.g., 250 KHz. A filler 514 may be positioned within the housing 504 and substantially surround the package 504, the half-cylinder piezoelectric transducer 502 and the metal backing 510. In one embodiment the filler 514 include at least one of: super epoxy, fluorinated oil such as Krytox® (Krytox is a registered trademark of E. I. DU PONT DE NEMOURS AND COMPANY), and silicon oil.

As shown by arrows 505 in FIG. 14, this configuration of the signal transmission device 500 ensures strong signal in a desired direction relative to the patient (e.g., laterally from patient) so that it can be picked up by the external interface device 305 and/or transceiver 307. In this half cylinder arrangement, metal backing 510 acts as reflector such that signals 505 are concentrated, e.g., within a 180 degree radius. Accordingly, strong signal strength can be achieved with less power relative to a full 360 degree arrangement. Note that while signal transmission device 500 includes a half-cylinder (i.e., 180 degree) piezoelectric transducer 502, other partial-cylinder transducers could likewise be utilized, e.g., a three-quarter cylinder transducer, a one quarter cylinder transducer, etc.

In still further embodiments, the piezoelectric transducer can have any cross-sectional shape that conforms to the implant housing, e.g., oval, rectangular, polygonal, etc. In such cases, the transducer can likewise be configured to directionally focus signals in a manner similar to the half piezo arrangement. For instance, a one third oval, half oval, etc., cross-section could be implemented to focus signals in a desired direction (i.e., less than 360 degrees). In still further cases, a phase array transducer arrangement could be implemented to channel signals in a desired direction.

Also positioned within the signal transmission device 500 is a printed circuit board 516. The printed circuit board 516 can include the controller 302 (FIGS. 4-9) thereon. Further, the printed circuit board 516 can include the switch 344 (FIGS. 4 and 8) and the sensor 346 (FIGS. 8-9) when used.

In an illustrative embodiment, external transceiver 307 of external interface device 305 may be placed laterally on a body part such as a leg. In this case, the external interface device 305 is an independent standalone device separate from an external adjustment device 400 that may be used at the same time. The transceiver can be configured to take up the different space than the external adjustment device 400, which, e.g., will be sitting anterior to the leg.

E. Energy Harvesting System

Figure 15:
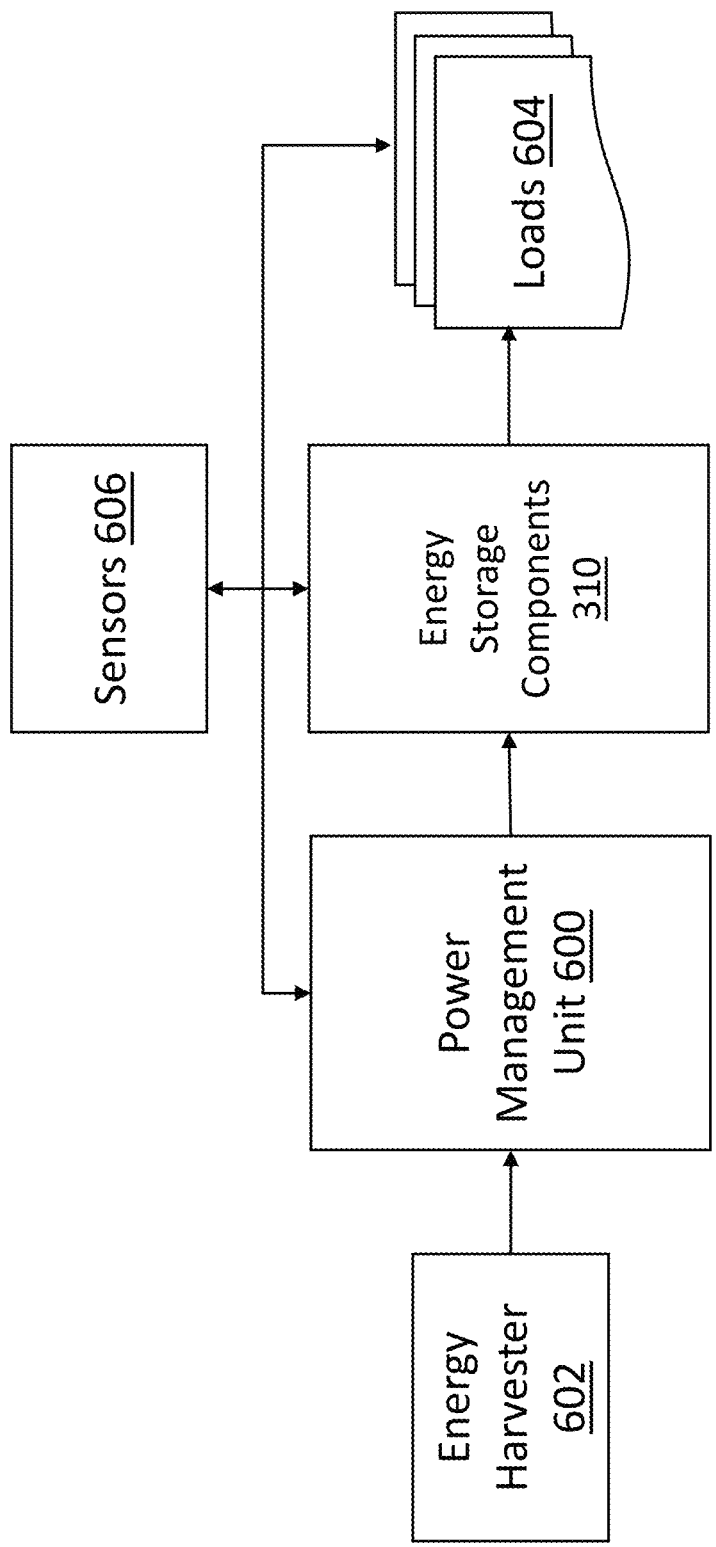
FIG. 15 shows a schematic of an energy harvesting system according to embodiments of the disclosure.

As shown in FIG. 15, in another embodiment, the implant 100 can include and energy harvesting system that captures energy, e.g., machinal energy, heat energy, etc., associated with the implant 100 and converts the energy to electrical energy. The system may include an energy harvesting component 602, a power management unit 600, energy storage components 310 and sensors 606. The energy storage components 310 may for example include a battery that supplies electricity to loads 604, such as the various smart components. Sensors 606 may be used to facilitate management of the system, e.g., determine amounts of energy being harvested, used, etc.

In one embodiment, a transducer 304 (FIG. 4) and/or half-cylinder piezoelectric transducer 502 (FIGS. 13 and 14) can be configured to harvest energy imparted on the implant 100 during movement of the patient having the implant 100 implanted therein. That is, the transducer 304, 502 itself acts as the energy harvesting component 602. In this embodiment, the power storage components 310 are configured to store energy harvested from the transducer 304. However, it is to be understood that an energy harvesting component 602 separate from the transducer 304 can be provided without departing from aspects of the disclosure such as, for example, a magnet and coil, an electromagnet, and a RF harvester. With further reference to FIG. 4, the energy harvested by the transducer 304 can be configured to provide power for at least one of the controller 302, the transducer 304, the load cell 306, one or more sensors 336, 346 and/or any other smart components of the implant 100. Wiring may couple the transducer 304 and the energy storage components 310 such that the energy harvested by the transducer 304 can be transferred to the energy storage components 310 and back to the transducer 304 to power the transducer 304 when needed. The wiring can include a printed circuit board having a power management unit 600 thereon configured to adjust a voltage of the energy harvested by the energy harvesting component. As shown in FIG. 15, the power management unit 600 collects the voltage signal from the energy harvesting component 602 (e.g., transducer 304, 502) and adjusts or modifies the voltage harvested to a level that can be stored within the energy storage components 310.

The energy harvesting component 602 is placed to capture the surrounding energy, e.g., vibration, electromagnetic, magnetic, heat, etc., and convert it into an electrical energy. Voltage is induced, e.g., when the transducer 304 is going through a strain. Often the voltage is in the format of AC swinging between negative and positive potentials. In one embodiment, a rectifier (is used to collect just the positive voltage, otherwise the positive and negative cancels out. To store the power efficiently into an energy format, the raw power is often regulated with a current flow manager. Switches are placed to traffic the inflow and outflow of electrical power to loads 604, such as one of the smart components. In the case where transducer 304 acts as the energy harvester, the same or another piezoelectric transducer may be used for communication, e.g., to induce ultrasound signals.

There is also wiring coupling the energy storage components 310 to the controller 302, sensors 336, 346 and load cell 306 such that the energy storage components 310 can supply the harvested energy to those components as well. As noted, the transducer 304 can be a piezoelectric transducer. In this embodiment, the transducer 304 is coupled to an internal surface of the housing 102. More specifically, the transducer 304 is coupled to an internal surface of the housing 102 at a location of the implant 100 that receives tension or compressive stresses due to movement of the patient. The transducer 304 harvests energy from stress generated by the implant 100 due to the bending force imparted on the implant 100 during movement of the patient. Therefore, in this embodiment, the implant 100 smart components are powered by the energy harvested directly from movement of the patient. In certain embodiments, the transducer 304, 502 can act as both a communication device and an energy harvesting device. In other embodiments, implant 100 includes a first transducer for communication and a second transducer for energy harvesting.

An illustrative method using energy harvesting includes implanting the implant 100 within a patient, such as for example within an intramedullary canal of a bone. An osteotomy is performed to create a first bone portion and a second bone portion. The housing 102 is coupled to the first bone portion and the adjustable portion 104 is coupled to the second bone portion. The method further includes harvesting energy from stresses imparted on the implant 100 during movement by the patient having the implant 100 implanted therein and using the harvested energy to power at least one of the smart components. As discussed herein, the energy harvesting system can include the transducer 304 configured to send data to an external interface device 305 (FIGS. 7 and 9) via transceiver 307 (FIGS. 7 and 9) positioned external to the patient. The data can include at least one of: a distraction force, a distraction force, a distraction length, a compression force, a compression torque, a compression length, a compressive stress, a tension stress, a biological condition, and a position of the implant 100. A medical professional can then view the data and determine treatment instructions (e.g., a distraction length, a distraction time, a distraction force, compression length, compression time, compression force) and send such instructions to the implant 100 and/or external adjustment device 400 via the external interface device 305. The implant 100 is adjusted such that adjustable portion 104 moves relative to the housing 102. Thus, the second bone portion moves relative to the first bone portion.

F. Reed Switch

In various embodiments, the implant 100 can include a switch 344 such as that shown in FIG. 4 for preserving power when one or more of the smart components are not in use. In one example, the switch 344 can include an electrical switch such as a reed switch that is operated by an applied magnetic field (such as from an external adjustment device 400 having at least one magnet 440 therein). In this example, the reed switch can be a normally-open reed switch that is configured to close or complete the circuit upon application of a magnetic field. The switch 344 can for example be configured to activate any component, e.g., the controller 302, transducer 304, load cell 306, sensors, etc., when the external adjustment device 400 (FIGS. 17-19) is in proximity to the adjustable implant 100. The switch 344 can be configured to activate (i.e., turn on) when a threshold distance between the adjustable implant 100 and the external adjustment device 400 is reached (e.g., 2-4 inches). The switch 344 can be configured to deactivate components when the external adjustment device 400 is farther than or outside of the threshold distance relative to the adjustable implant 100 such that an activatable component is in a resting or off state when the external adjustment device 400 is farther than the threshold distance relative to the adjustable implant 100. The switch 344 is operatively coupled to the activatable components via wiring (not shown). The switch 344 can be utilized in conjunction with a power management system for some or all the components in the implant 100 that require power supply components 310. In certain embodiments, the reed switch 344 can be configured to activate the controller 302, and the controller 302 can in turn manage power for other smart components (e.g., turn them on and off as needed).

An illustrative method involving a reed switch includes providing the implant 100 including the housing 102 and the adjustable portion 104 moveable relative to the housing 102 upon application of a force supplied by an external adjustment device 400, a sensor 336 configured to sense monitor a position of the actuator 121 of the adjustable implant 100, and a controller 302 disposed within the housing 102 and communicatively coupled to the sensor 336. The method also includes implanting the implant 100 within a patient, such as for example within an intramedullary canal of a bone. An osteotomy is performed to create a first bone portion and a second bon portion. The housing 102 is coupled to the first bone portion and the adjustable portion 104 is coupled to the second bone portion. The method also includes activating at least one of the controller 302, transducer 304 and/or sensors when the external adjustment device 400 is within a threshold proximity to the implant 100. The method also includes deactivating the at least one of the controller 302, transducer 304, and/or sensors when the external adjustment device 400 is outside of a threshold proximity to the implant 100. In one embodiment, once activated via the reed switch when the external adjustment device 400 is within the threshold proximity, the sensor 336 senses the angular position of the actuator 121. The controller 302 is configured to receive the angular position data from the sensor 336 and digitize the data when the external adjustment device 400 is within the threshold proximity. The controller 302 is also configured to send the digitized data to the transducer 304 when the external adjustment device 400 is in proximity to the implant 100. In one embodiment, the transducer 304 is configured to communicate with the external interface device 305 via radiofrequency waves. In another embodiment, the transducer 304 is configured to communicate with the external interface device via ultrasound waves. The transducer 304 communicates the at least one of the distraction force, distraction torque, distraction length, compression force, compression torque, and compression length when the external adjustment device 400 is within a threshold distance relative to the adjustable implant.

G. External Interface Device

Figure 16:
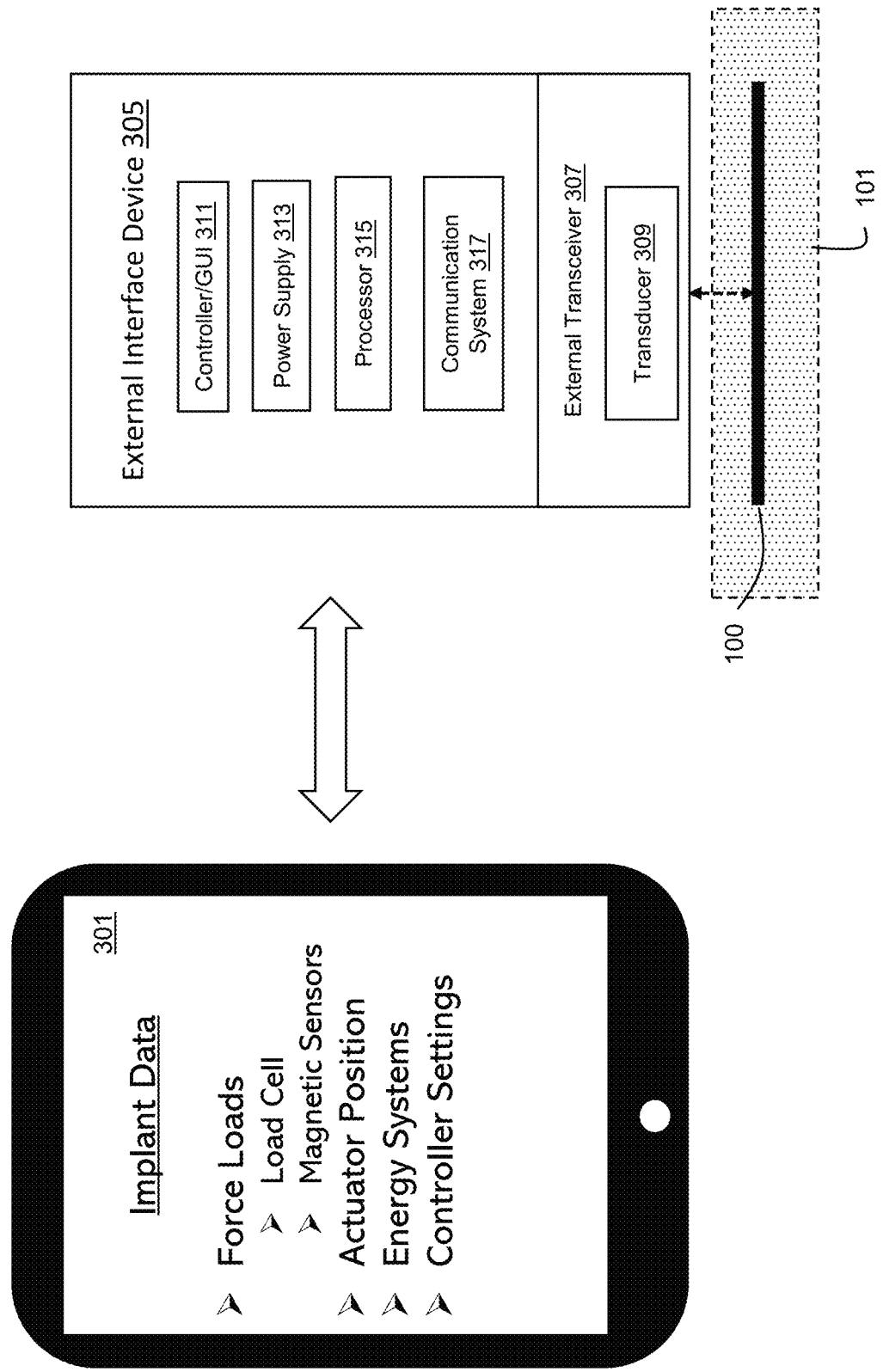
FIG. 16 shows an illustrative external interface device.

FIG. 16 depicts an illustrative external interface device 305 configured to interact with implant device 100 implanted in body 101. The external interface device 305 may comprise a handheld device that can be placed on or near the skin of a patient to allow a user to interact with (e.g., communicate, control, etc.) the controller in implant 100, e.g., via a transducer 304, 502. In certain embodiments, device 305 may include an external transceiver 307 configured to communicate (i.e., receive data and transmit data) with the implant 100. In certain embodiments, the transceiver 307 includes a transducer 309 capable of receiving or sending ultrasonic signals to and from a transducer 304, 502 in the implant 100. Device 305 may also include, e.g., a controller/GUI 311 that allows the operator to control and interact with the device 305, one or more power supply components 313, a processor 315, and a communication system 317. The external transceiver 307 may be configured to communicate, for example, via ultrasound, radiofrequency, or other types of signals. In the case where ultrasound is used, the transducer 309 can include any of the types of transducers discussed relative to the transducer 304, 502. The controller 311 is configured to manage the external interface device 305 and can include any of the types of controllers discussed relative to the controller 302 (FIG. 4). The power supply components 313 are configured to supply power for the external interface device 305 and can include any of the power supply components discussed relative to the power supply components 310 (FIG. 4). Device 305 may be configured to interface with a smart device 301 (e.g., a smart phone, tablet, laptop, etc.) that allows a user to view and manage information transmitted from the implant via device 305, including data generated by smart components. Smart device 301 may also be configured to send data and commands to the implant 100 via device 305. The smart device 301 may be implemented with a downloadable App. The smart device 301 allows for the patient or medical professional to easily interact with the implant 100 and external interface device 305. In some embodiments, the features of smart device 301 and external interface device 305 are integrated into a single device.

III. General External Adjustment Device Discussion

Actuation of the actuator 121 can be caused and controlled by an external adjustment device such as those described in U.S. Pat. No. 8,382,756 filed on Nov. 20, 2009, U.S. Pat. No. 9,248,043 filed Jun. 29, 2011, U.S. Pat. No. 9,078,711 filed on Jun. 6, 2012, U.S. Pat. No. 9,044,281 filed on Oct. 18, 2012, U.S. application Ser. No. 13/172,598 filed on Jun. 29, 2011, U.S. application Ser. No. 14/698,665 filed on Apr. 28, 2015, U.S. application Ser. No. 14/932,904 filed on Nov. 4, 2015, U.S. Ser. No. 16/004,099 filed on Dec. 12, 2016, and App. No. PCT/US2020/017338 filed on Feb. 7, 2020, all of which are incorporated herein by reference as if set forth in their entirety. external interface device 305

The external adjustment device 400, may include a housing 401 having a handle 402 and a display 403. The handle 402 is shown extending upwardly from the housing 401. In some embodiments, the display 403 may be integrated with the housing 401 of the external adjustment device 400. In the illustrated embodiment, the external adjustment device 400 is configured to receive a removable controller 410 having a display 403, with the display 403 being an integral part of the removable controller 410.

According to an exemplary embodiment, the controller 410 may be a handheld electronic device. The handheld electronic device may be, for example, a smartphone, a tablet, and any other known handheld electronic device. The handheld electronic device may contain and may be operatively connected to a display and/or one or more wireless communication protocols (e.g., Wi-Fi or Bluetooth®). The display of the handheld electronic device may be disposed adjacent to a top surface of the external adjustment device 400, such that the display 403 can communicate information to and receive instructions from a user during use.

For example, in some embodiments the display 403 may present to a user a graphical user interface (GUI). The display 403 may include one or more of a touchscreen or touchscreen technology, including, for example, capacitive touchscreen technology. The GUI may communicate adjustment instructions to a user which may correspond to a treatment regimen to guide the user in adjusting the adjustable implant in accordance with the treatment regimen. Additionally, the GUI may include one or more touchscreen digital buttons configured to activate and control the external adjustment device 400.

FIG. 17 shows a front view of the external adjustment device 400, the external adjustment device 400 including a power supply input 422 and a data connection port 412. Additionally, a bottom surface of the housing 401 is shown including a curvature configured to form to a patient's body and minimize a distance (GAP) between the magnet 440 and a magnet 118 (FIG. 3) of the adjustable implant 100 (FIG. 14). The power supply input 422 may be configured to removably receive an AC power supply. The data connection port 412 may be configured to removably receive a data communication cable. The data communication cable may be configured to connect the external adjustment device 400 to a tertiary device to one or more of update the controller 410 software and download data from the controller 410.

FIG. 18 shows a cross-sectional side view of the external adjustment device 400 in accordance with the first embodiment. The external adjustment device 400 shown including the housing 401, the controller 410, an internal power storage device 420, a motor 430, and at least one magnet 440.

The internal power storage device 420 and wireless communication capabilities of the controller 440, may provide for wireless operation of the external adjustment device 400. The internal power storage device 420 may negate the need for a power chord during operation. The controller 410 may provide a low voltage control system negating the need for a bulky external control module. And wireless communication capabilities, for example one or more of RF, Wi-Fi Bluetooth® may enable the external adjustment device 400 and the controller 410 for remote operation. The remote operation may be achieved by one or more of a tertiary device in the same room, and across the internet by a tertiary device on the other side of the globe.

In some embodiments, the controller 410 may be a control board disposed within the housing 401 of the external adjustment device 400. The display 403 may include any type of display 403, including for example: LED, LCD, OLED, and any other known display and touchscreen technology. The control interface board 411 may contain or be in communication with one or more communication circuit, for example, one or more of Wi-Fi, cellular networks, or Bluetooth®, enabling communication between the external adjustment device 400 and one or more tertiary devices.

In FIG. 18, the controller 410 is shown operably connected to a controller interface board 411 by at least one interconnect. In some embodiments, this connection may be established via a physical connection as illustrated, and in some embodiments, a wireless connection, for example, Bluetooth®. The control interface board 411 may be further connected to one or more of a power interface board 421, the power storage device 420, and the actuator 430.

The controller 410 may be remotely accessible and remotely controllable by a tertiary device allowing for remote operation of the external adjustment device 400 by a user from outside of a sterile field.

The external adjustment device 400 is also shown including an internal power storage device 420. The power storage device 420 may include a battery, a capacitor, and any other power storage device known and used in the art. The power storage device may be rechargeable and the external adjustment device 400 may include a recharging circuit configured to recharge the power storage device 420 using an external power source. The external power source, for example a power supply, may be operably connected to the recharging circuit of the power storage device via the power supply input. The power storage device 420, and/or at least a portion of the recharging circuit, may be disposed adjacent to a surface of the external adjustment device 400, enabling connection of a power supply charge cable to the external adjustment device 400. In some embodiments, the recharging circuit may enable wireless charging of the internal power storage device 420, using induction to wirelessly transfer power. In some embodiments, the recharging circuit may be part of and connected to one or more of the power distribution board 421 and the power storage device 400.

In the illustrated embodiment, the power storage device 420 is a battery. The battery 420 is mounted to a chassis of the external adjustment device 400, adjacent to a surface of the external adjustment device 400 enabling connection of a power supply to the external adjustment device 400 at a power supply input 422. The battery 420 includes a power interface board 421, configured to interface with and communicate power to the motor 430. The power interface board 421 may be operably coupled to one or more of the motor 430 and the control interface board 411. The power interface board 421 may also communicate electrical energy from one or more of a power supply input 422 and the power storage device 420, to the controller 410.

The actuator of the external adjustment device 400 includes an electronic motor 430. The driver of the external adjustment device 400 includes a magnet 440 rotatably coupled to the electronic motor 430. The motor 430 may be operably connected to one or more of the controller 410, the control interface board 411, the power interface board 421 and the internal power storage device 420. In the illustrated embodiment the electronic motor 430 is operably connected to the internal power storage device 420 by the power interface board 421. The power interface board 421 may include power distribution circuits to communicate electrical energy to the electronic motor 430 from one or more of the power supply input 422 and the internal power storage device 420. The power interface board 421 may also be operably connected to the control interface board 411, to relay control information from the controller 410 to the motor 430. In some embodiments, the controller 410 may be in direct communication with the motor 430, and in some embodiments the controller 410 may be connected to the electronic motor via a wireless connection, for example a Bluetooth® connection.

The motor 430 may include any type of motor capable of rotating the magnet 440. The motor 430 is an electric motor and may include a rotational speed sensor 432. The rotational speed sensor 432 connected to and in communication with one or more of the control interface board 411 and the controller 410. In some embodiments, the internal speed sensor 432 may include for example one or more of an encoder and a digital output of an electronic motor. In some embodiments, the motor 430 is configured to communicate rotational speed data to the controller 410 wirelessly.

FIG. 19 shows an enhanced cross-sectional view of the motor 430 and the magnet 440 of the external adjustment device 400 in accordance with a first embodiment. The magnet 440 is shown rotatably coupled to the motor 430 by one or more couplings 431. In the illustrated embodiment, the magnet 440 includes an internal cavity 441 having an internal surface 442 and having a tapered profile. A magnet drive shaft 433 is shown including a magnet contact surface 434 having a tapered profile. The tapered profile of the magnet drive shaft 433 is configured to communicate with the tapered profile of the internal surface 442 of the magnet 440. This enables the magnet 440 to be secured to the magnet drive shaft 433 by a friction fit, the magnet 440 configured to be held onto the magnet drive shaft 433 by a cap 435 and the communicating tapered profiles. In some embodiments, the magnet 440 may be attached to the magnet drive shaft 433 using an adhesive material.

The magnet 440 may comprise any magnetic element including a radially polarized cylindrical magnet, a permanent magnet, an electromagnet, and any other magnetic element known and used in the art. The magnet 440 is configured to magnetically couple with a permanent magnet 118 of an adjustable implant 100 and to rotate the permanent magnet 118 and adjust the adjustable implant 100. Upon a rotation of the magnet 440, a rotating magnetic field will be generated, placing a force on the magnetically coupled permanent magnet 118 of the adjustable implant 100, thereby inducing a rotation of the permanent magnet 118 and subsequent adjustment of the adjustable implant 100.

In some embodiments, the external adjustment device 400 includes one or more sensors configured to monitor a rotational speed of the magnet 440. In some embodiments, the sensors include magnetic sensors, for example Hall-Effect sensors disposed on one or more of the housing 401, a plate, and a chassis, and may be placed adjacent to the magnet 440. In some embodiments, the sensors include photo-sensors. The magnet may include one or more circular optical encoder strips to work in conjunction with the photo-sensors. U.S. patent application Ser. No. 14/932,904 describes various systems and methods for non-invasively detecting the force generated by a non-invasively adjustable implant, the entire contents of which are hereby incorporated by reference.

In the illustrated embodiment the external adjustment device 400 includes a motor 430 having one or more rotational speed sensor 432 configured to detect a change in a motor angular velocity (V), and thereby as described below non-invasively detect a rotation of the permanent magnet 118 of the adjustable implant 100. The motor 430 has torque characteristics that allows for little variation in motor angular velocity (V) during a motor rotation and corresponding magnet 440 rotation, when there is no implant or ferrous material located near the ERC magnet or magnetically coupled to the magnet 440.

When an adjustable implant 100 having a magnet 118 is in close proximity to the rotating magnet 440, and for example magnetically coupled to the magnet 440, the magnetic poles of both magnets cause a changing load on the motor 430 twice per revolution. This causes the magnet 440 to increase or decrease in angular velocity, with the variations detectable by the rotational speed sensor 432.

One or more example computing environments 100 can be used to implement techniques described herein. The computing environment 100 is a set of one or more virtual or physical computers configured to cause output based on data. In many examples, the computing environment 100 is a workstation, desktop computer, laptop computer, server, mobile computer, smartphone, tablet, embedded computer, other computers, or combinations thereof. In other examples, the computing environment is a virtual machine, group of computers, other computing environments, or combinations thereof.

In the illustrated example, the computing environment 1000 includes one or more processors 1010, memory 1020, and an interface 1030 coupled to a network 1002. The network 1002 is a group of communicatively coupled computing environments and associated hardware, such as a local area network, the Internet, other networks, or combinations thereof.

The one or more processors 1010 are one or more physical or virtual components configured to obtain and execute instructions. In many examples, the one or more processors 1010 are central processing units, but can take other forms such as microcontrollers, microprocessors, graphics processing units, tensor processing units, other processors, or combinations thereof.

The memory 1020 is one or more physical or virtual components configured to store information, such as data or instructions. In some examples, the memory 1020 includes the computing environment's main memory (e.g., random access memory) or long-term storage memory (e.g., a solid state drive). The memory can be transitory or non-transitory computer-readable or processor-readable storage media.

The interface 1030 is a set of one or more components by which the computing environment 1000 can provide output or receive input. For example, the interface 1030 can include one or more user input components, such as one or more sensors, buttons, pointers, keyboards, mice, gesture controls, touch controls (e.g., touch-sensitive strips or touch screens), eye trackers, voice recognition controls (e.g., microphones coupled to appropriate natural language processing components), other user input components, or combinations thereof. The interface 1030 can include one or more user output components, such as one or more lights, displays, speakers, haptic feedback components, other user output components, or combinations thereof. The interface 1030 can further include one or more components configured to provide output to or receive input from other devices, such as one or more ports (e.g., USB ports, THUNDERBOLT ports, serial ports, parallel ports, Ethernet ports) or wireless communication components (e.g., components configured to communicate according to one or more radiofrequency protocols, such as WI-FI, BLUETOOTH, ZIGBEE, or other protocols).

The computing environment 1000 can include one or more additional components or connections among components (e.g., busses).

The computing environment 1000 can be configured to implement one or more aspects described herein. Algorithms, steps, or procedures for so configuring the computing environment and performing functions described herein can be understood from the description herein in view of knowledge in the art of how to implement computer functions.

The computing environment 1000 can be configured to implement one or more aspects described herein. Algorithms, steps, or procedures for so configuring the computing environment and performing functions described herein can be understood from the description herein in view of knowledge in the art of how to implement computer functions.

Example techniques for implementing such computer functions include frameworks and technologies offering a full stack of plug-and-play capabilities for implementing desktop and browser-based applications (e.g., the applications implementing aspects described herein). The frameworks can provide a desktop web application featuring or using an HTTP server such as NODEJS or KATANA and an embeddable web browser control such as the CHROMIUM EMBEDDED FRAMEWORK or the JAVA/.NET CORE web view. The client-side frameworks can extend that concept by adding plug-and-play capabilities to desktop and the web shells for providing apps capable of running both on the desktop and as a web application. One or more components can be implemented using a set of OWIN (Open Web Interface for .NET) components built by MICROSOFT targeting the traditional .NET runtime. KATANA, and by definition OWIN, allow for chaining together middleware (OWIN-compliant modules) into a pipeline thus offering a modular approach to building web server middleware. For instance, the client-side frameworks can use a Katana pipeline featuring modules such as SIGNALR, security, an HTTP server itself. The plug-and-play capabilities can provide a framework allowing runtime assembly of apps from available plugins. An app built atop of a plug-and-play framework can have dozens of plugins, with some offering infrastructure-level functionality and other offering domain-specific functionality. The CHROMIUM EMBEDDED FRAMEWORK is an open source framework for embedding the CHROMIUM browser engine with bindings for different languages, such as C# or JAVA. OWIN is a standard for an interface between .NET web applications and web servers aiming at decoupling the relationship between ASP.NET applications and IIS by defining a standard interface.

Further example techniques for implementing such computer functions or algorithms include frameworks and technologies provided by or in conjunction with programming languages and associated libraries. For example, languages such as C, C++, C#, PYTHON, JAVA, JAVASCRIPT, RUST, assembly, HASKELL, other languages, or combinations thereof can be used. Such languages can include or be associated with one or more standard libraries or community provided libraries. Such libraries in the hands of someone skilled in the art can facilitate the creation of software based on descriptions herein, including the receiving, processing, providing, and presenting of data. Example libraries for PYTHON and C++ include OPENCV (e.g., which can be used to implement computer vision and image processing techniques), TENSORFLOW (e.g., which can be used to implement machine learning and artificial intelligence techniques), and GTK (e.g., which can be used to implement user interface elements). Further examples include NUMPY for PYTHON (e.g., which can be used to implement data processing techniques). In addition, other software can provide application programming interfaces that can be interacted with to implement one or more aspects described herein. For example, an operating system for the computing environment (e.g., WINDOWS by MICROSOFT CORP., MACOS by APPLE INC., or a LINUX-based operating system such as UBUNTU by CANONICAL LTD.) or another component herein (e.g., an operating system of a robot, such as IIQKA.OS or SUNRISE.OS by KUKA ROBOTICS CORPORATION where the robot is a model of KUKA ROBOTICS CORPORATION) can provide application programming interfaces or libraries to usable to implement aspects described herein. As a further example, a provider of a navigation system, laser console, wireless card, display, motor, sensors, or another component may not only provide hardware components (e.g., sensor, a camera, wireless card, motor, or laser generator), but also software components (e.g., libraries, drivers, or applications) usable to implement features with respect to the components.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced items. It will be further understood that the terms "comprises" and/or comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. An adjustable implant configured to be implanted into a patient, the adjustable implant comprising:
   a housing;
   an adjustable portion moveable relative to the housing;
   a load cell within the housing for measuring a load imparted on the implant during movement of the adjustable portion relative to the housing or during movement of a bone relative to the housing;
   apertures within the housing for receiving bone anchors therein; and
   a controller within the housing and configured to determine at least one of a distraction force and a compression force based on the load measured by the load cell;
   wherein the load cell includes apertures therein corresponding to the apertures within the housing for receiving the bone anchors therein to couple the load cell to the bone.

2. The adjustable implant of claim 1, wherein the load cell includes at least one sensor.

3. The adjustable implant of claim 1, wherein the load cell is coupled with the housing.

4. The adjustable implant of claim 3, wherein the load cell is coupled with the housing via a pin.

5. The adjustable implant of claim 1, further comprising: wiring coupling the load cell and the controller.

6. The adjustable implant of claim 5, further comprising: a polymer housing surrounding the wiring within the housing.

7. The adjustable implant of claim 1, further comprising: a transducer configured to send the at least one of the distraction force and the compression force to an external interface device.

8. The adjustable implant of claim 1, wherein the apertures of the load cell have a smaller diameter than a diameter of the apertures within the housing.

9. The adjustable implant of claim 1, wherein the load cell includes a first strain gauge and a second strain gauge.

10. The adjustable implant of claim 1, further comprising a reed switch configured to power on the controller in response to an external device being within a threshold distance of the adjustable implant and power off the controller in response to the external device being outside the threshold distance of the adjustable implant.

11. The adjustable implant of claim 1, further comprising:
    an actuator configured to cause movement of the adjustable portion relative to the housing; and
    a sensor configured to determine an amount of rotation of the actuator.

12. The adjustable implant of claim 11, further comprising:
    a controller configured to digitize data acquired by the load cell and modulate the data into an ultrasound signal; and
    a transducer configured to send the ultrasound signal comprising the digitized data to an external interface device.

13. The adjustable implant of claim 12, wherein the data includes at least one of: the load imparted on the implant, a distraction length of the implant, a compression length of the implant, a distraction force of the implant, and a compression force of the implant.

14. An adjustable implant configured to be implanted into a patient, the adjustable implant comprising:
    a housing;
    an adjustable portion moveable relative to the housing;
    a load cell within the housing for measuring a load imparted on the implant during movement of the adjustable portion relative to the housing or during movement of a bone relative to the housing;
    apertures within the housing for receiving bone anchors therein;

an actuator configured to cause movement of the adjustable portion relative to the housing;

a controller configured to digitize data acquired by the load cell and modulate the data into a signal; and a transducer configured to send the signal encoding the digitized data to an external interface device;

wherein the load cell includes apertures therein corresponding to the apertures within the housing for receiving the bone anchors therein to couple the load cell to the bone.

15. The adjustable implant of claim 14, wherein the signal comprises an ultrasound signal.

16. The adjustable implant of claim 14, further comprising a sensor configured to determine an amount of rotation of the actuator.

17. The adjustable implant of claim 14, wherein the load cell is coupled with the housing.

18. The adjustable implant of claim 17, wherein the load cell is coupled with the housing via a pin.

19. The adjustable implant of claim 14, wherein the controller is configured to determine at least one of a distraction force and a compression force based on the load measured by the load cell.

20. The adjustable implant of claim 19, further comprising:

wiring coupling the load cell and the controller.

21. The adjustable implant of claim 20, further comprising:

a polymer housing surrounding the wiring within the housing.

22. The adjustable implant of claim 19, wherein the transducer is configured to send the at least one of the distraction force and the compression force to the external interface device.

23. The adjustable implant of claim 14, wherein the apertures of the load cell have a smaller diameter than a diameter of the apertures within the housing.

24. The adjustable implant of claim 14, wherein the load cell includes a first strain gauge and a second strain gauge.

25. The adjustable implant of claim 14, further comprising a reed switch configured to power on the controller in response to an external device being within a threshold distance of the adjustable implant and power off the controller in response to the external device being outside the threshold distance of the adjustable implant.

26. The adjustable implant of claim 14, wherein the data includes at least one of: the load imparted on the implant, a distraction length of the implant, a compression length of the implant, a distraction force of the implant, and a compression force of the implant.

27. An adjustable implant configured to be implanted into a patient, the adjustable implant comprising:

a housing;

an adjustable portion moveable relative to the housing;

a load cell within the housing for measuring a load imparted on the implant during movement of the adjustable portion relative to the housing or during movement of a bone relative to the housing;

apertures within the housing for receiving bone anchors therein;

an actuator configured to cause movement of the adjustable portion relative to the housing;

a sensor configured to determine an amount of rotation of the actuator;

a controller configured to digitize data acquired by the load cell and modulate the data into an ultrasound signal; and a transducer configured to send the ultrasound signal comprising the digitized data to an external interface device.

28. The adjustable implant of claim 27, wherein the load cell includes apertures therein corresponding to the apertures within the housing for receiving the bone anchors therein to couple the load cell to the bone.

29. The adjustable implant of claim 28, wherein the apertures of the load cell have a smaller diameter than a diameter of the apertures within the housing.

30. The adjustable implant of claim 27, wherein the load cell is coupled with the housing.

31. The adjustable implant of claim 30, wherein the load cell is coupled with the housing via a pin.

32. The adjustable implant of claim 27, wherein the controller is configured to determine at least one of a distraction force and a compression force based on the load measured by the load cell.

33. The adjustable implant of claim 32, further comprising:

wiring coupling the load cell and the controller.

34. The adjustable implant of claim 33, further comprising:

a polymer housing surrounding the wiring within the housing.

35. The adjustable implant of claim 32, wherein the transducer is configured to send the at least one of the distraction force and the compression force to the external interface device.

36. The adjustable implant of claim 27, wherein the load cell includes a first strain gauge and a second strain gauge.

37. The adjustable implant of claim 27, further comprising a reed switch configured to power on the controller in response to an external device being within a threshold distance of the adjustable implant and power off the controller in response to the external device being outside the threshold distance of the adjustable implant.

38. The adjustable implant of claim 27, wherein the data includes at least one of: the load imparted on the implant, a distraction length of the implant, a compression length of the implant, a distraction force of the implant, and a compression force of the implant.

* * * * *